US012788495B2

(12) United States Patent
Xu et al.

(10) Patent No.: US 12,788,495 B2
(45) Date of Patent: Nov. 10, 2026

(54) SYSTEMS AND METHODS FOR ROBOTICALLY-ASSISTED HISTOTRIPSY TARGETING BASED ON MRI/CT SCANS TAKEN PRIOR TO TREATMENT

(71) Applicant: THE REGENTS OF THE UNIVERSITY OF MICHIGAN, Ann Arbor, MI (US)

(72) Inventors: Zhen Xu, Ann Arbor, MI (US); Aditya S. Pandey, Ann Arbor, MI (US); Jonathan Sukovich, Ann Arbor, MI (US); Tyler Gerhardson, Ann Arbor, MI (US); Sang Won Choi, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 389 days.

(21) Appl. No.: 17/790,975

(22) PCT Filed: Jan. 7, 2021

(86) PCT No.: PCT/US2021/012455
§ 371 (c)(1),
(2) Date: Jul. 6, 2022

(87) PCT Pub. No.: WO2021/142090
PCT Pub. Date: Jul. 15, 2021

(65) Prior Publication Data

US 2023/0038498 A1 Feb. 9, 2023

Related U.S. Application Data

(60) Provisional application No. 62/958,209, filed on Jan. 7, 2020.

(51) Int. Cl.
*A61B 34/20* (2016.01)
*A61B 34/30* (2016.01)
(Continued)

(52) U.S. Cl.
CPC .............. *A61B 34/20* (2016.02); *A61B 34/30* (2016.02); *A61N 7/00* (2013.01);
(Continued)

(58) Field of Classification Search
CPC ... A61B 8/5261; A61B 6/5247; A61B 6/5235; A61N 7/00
See application file for complete search history.

(56) References Cited

U.S. PATENT DOCUMENTS

| | | | |
|---|---|---|---|
| 3,243,497 | A | 3/1966 | Kendall et al. |
| 3,679,021 | A | 7/1972 | Goldberg et al. |

(Continued)

FOREIGN PATENT DOCUMENTS

| | | | |
|---|---|---|---|
| AU | 2017222925 | B2 | 11/2021 |
| BR | 112018017326 | B1 | 12/2022 |

(Continued)

OTHER PUBLICATIONS

Stopek ; U.S. Appl. No. 17/904,326 entitled "Minimally invasive histotripsy systems and methods," filed Aug. 16, 2022.

(Continued)

*Primary Examiner* — Pascal M Bui Pho
(74) *Attorney, Agent, or Firm* — Shay Glenn LLP

(57) ABSTRACT

Methods and devices for producing cavitation in tissue are provided. Methods and devices are also provided for surgical navigation, including defining a target treatment zone and navigating a focus of a therapy transducer to the target treatment zone. Embodiments are provided for co-registering a plurality of surgical imaging and navigation systems. Systems for performing Histotripsy therapy are also discussed.

16 Claims, 6 Drawing Sheets

(51) Int. Cl.
*A61B 90/00* (2016.01)
*A61N 7/00* (2006.01)

(52) U.S. Cl.
CPC ................ *A61B 2034/2051* (2016.02); *A61B 2034/2055* (2016.02); *A61B 2034/2063* (2016.02); *A61B 2090/364* (2016.02); *A61B 2090/3762* (2016.02); *A61B 2090/3983* (2016.02)

(56) References Cited

U.S. PATENT DOCUMENTS

| | | | |
|---|---|---|---|
| 3,693,415 | A | 9/1972 | Whittington |
| 3,879,699 | A | 4/1975 | Pepper |
| 4,016,749 | A | 4/1977 | Wachter |
| 4,024,501 | A | 5/1977 | Herring et al. |
| 4,051,394 | A | 9/1977 | Tieden |
| 4,114,457 | A | 9/1978 | Thun |
| 4,117,446 | A | 9/1978 | Alais |
| 4,266,747 | A | 5/1981 | Souder, Jr. et al. |
| 4,269,174 | A | 5/1981 | Adair |
| 4,277,367 | A | 7/1981 | Madsen et al. |
| 4,351,038 | A | 9/1982 | Alais |
| 4,406,153 | A | 9/1983 | Ophir et al. |
| 4,440,025 | A | 4/1984 | Hayakawa et al. |
| 4,447,031 | A | 5/1984 | Souder, Jr. et al. |
| 4,453,408 | A | 6/1984 | Clayman |
| 4,483,343 | A | 11/1984 | Beyer et al. |
| 4,483,345 | A | 11/1984 | Miwa |
| 4,548,374 | A | 10/1985 | Thompson et al. |
| 4,549,533 | A | 10/1985 | Cain et al. |
| 4,550,606 | A | 11/1985 | Drost |
| 4,551,794 | A | 11/1985 | Sandell |
| 4,575,330 | A | 3/1986 | Hull |
| 4,622,972 | A | 11/1986 | Giebeler, Jr. |
| 4,625,731 | A | 12/1986 | Quedens et al. |
| 4,641,378 | A | 2/1987 | McConnell et al. |
| 4,669,483 | A | 6/1987 | Hepp et al. |
| 4,689,986 | A | 9/1987 | Carson et al. |
| 4,757,820 | A | 7/1988 | Itoh |
| 4,791,915 | A | 12/1988 | Barsotti et al. |
| 4,819,621 | A | 4/1989 | Ueberle et al. |
| 4,829,491 | A | 5/1989 | Saugeon et al. |
| 4,856,107 | A | 8/1989 | Dory |
| 4,865,042 | A | 9/1989 | Umemura et al. |
| 4,888,746 | A | 12/1989 | Wurster et al. |
| 4,890,267 | A | 12/1989 | Rudolph |
| 4,922,917 | A | 5/1990 | Dory |
| 4,928,672 | A | 5/1990 | Grasser et al. |
| 4,938,217 | A | 7/1990 | Lele |
| 4,957,099 | A | 9/1990 | Hassler |
| 4,973,980 | A | 11/1990 | Howkins et al. |
| 4,984,575 | A | 1/1991 | Uchiyama et al. |
| 4,991,151 | A | 2/1991 | Dory |
| 4,995,012 | A | 2/1991 | Dory |
| RE33,590 | E | 5/1991 | Dory |
| 5,014,686 | A | 5/1991 | Schafer |
| 5,065,751 | A | 11/1991 | Wolf |
| 5,078,140 | A | 1/1992 | Kwoh |
| 5,080,101 | A | 1/1992 | Dory |
| 5,080,102 | A | 1/1992 | Dory |
| 5,091,893 | A | 2/1992 | Smith et al. |
| 5,092,336 | A | 3/1992 | Fink |
| 5,097,709 | A | 3/1992 | Masuzawa et al. |
| 5,111,822 | A | 5/1992 | Dory |
| 5,143,073 | A | 9/1992 | Dory |
| 5,143,074 | A | 9/1992 | Dory |
| 5,150,711 | A | 9/1992 | Dory |
| 5,158,070 | A | 10/1992 | Dory |
| 5,158,071 | A | 10/1992 | Umemura et al. |
| 5,163,421 | A | 11/1992 | Bernstein et al. |
| 5,165,412 | A | 11/1992 | Okazaki |
| 5,174,294 | A | 12/1992 | Saito et al. |
| 5,195,509 | A | 3/1993 | Rentschler et al. |
| 5,209,221 | A | 5/1993 | Riedlinger |
| 5,215,680 | A | 6/1993 | D'Arrigo |
| 5,219,401 | A | 6/1993 | Cathignol et al. |
| 5,222,806 | A | 6/1993 | Roberts |
| 5,230,340 | A | 7/1993 | Rhyne |
| 5,295,484 | A | 3/1994 | Marcus et al. |
| 5,316,000 | A | 5/1994 | Chapelon et al. |
| 5,354,258 | A | 10/1994 | Dory |
| 5,380,411 | A | 1/1995 | Schlief |
| 5,393,296 | A | 2/1995 | Rattner |
| 5,409,002 | A | 4/1995 | Pell |
| 5,431,621 | A | 7/1995 | Dory |
| 5,435,311 | A | 7/1995 | Umemura et al. |
| 5,443,069 | A | 8/1995 | Schaetzle |
| 5,450,305 | A | 9/1995 | Boys et al. |
| 5,469,852 | A | 11/1995 | Nakamura et al. |
| 5,474,071 | A | 12/1995 | Chapelon et al. |
| 5,474,531 | A | 12/1995 | Carter |
| 5,490,051 | A | 2/1996 | Messana |
| 5,492,126 | A | 2/1996 | Hennige et al. |
| 5,501,655 | A | 3/1996 | Rolt et al. |
| 5,520,188 | A | 5/1996 | Hennige et al. |
| 5,523,058 | A | 6/1996 | Umemura et al. |
| 5,524,620 | A | 6/1996 | Rosenschein |
| 5,524,875 | A | 6/1996 | Thommen, Jr. |
| 5,540,909 | A | 7/1996 | Schutt |
| 5,542,935 | A | 8/1996 | Unger et al. |
| 5,558,092 | A | 9/1996 | Unger et al. |
| 5,563,346 | A | 10/1996 | Bartelt et al. |
| 5,566,675 | A | 10/1996 | Li et al. |
| 5,573,497 | A | 11/1996 | Chapelon |
| 5,580,575 | A | 12/1996 | Unger et al. |
| 5,582,578 | A | 12/1996 | Zhong et al. |
| 5,590,657 | A | 1/1997 | Cain et al. |
| 5,601,526 | A | 2/1997 | Chapelon et al. |
| 5,617,862 | A | 4/1997 | Cole et al. |
| 5,648,098 | A | 7/1997 | Porter |
| 5,665,054 | A | 9/1997 | Dory |
| 5,666,954 | A | 9/1997 | Chapelon et al. |
| 5,676,452 | A | 10/1997 | Scholz |
| 5,676,692 | A | 10/1997 | Sanghvi et al. |
| 5,678,554 | A | 10/1997 | Hossack et al. |
| 5,683,064 | A | 11/1997 | Copeland et al. |
| 5,694,936 | A | 12/1997 | Fujimoto et al. |
| 5,695,460 | A | 12/1997 | Siegel et al. |
| 5,717,657 | A | 2/1998 | Ruffa |
| 5,720,287 | A | 2/1998 | Chapelon et al. |
| 5,724,972 | A | 3/1998 | Petrofsky |
| 5,743,863 | A | 4/1998 | Chapelon |
| 5,753,929 | A | 5/1998 | Bliss |
| 5,759,162 | A | 6/1998 | Oppelt et al. |
| 5,766,138 | A | 6/1998 | Rattner |
| 5,769,790 | A | 6/1998 | Watkins et al. |
| 5,797,848 | A | 8/1998 | Marian et al. |
| 5,820,623 | A | 10/1998 | Ng |
| 5,823,962 | A | 10/1998 | Schaetzle et al. |
| 5,827,204 | A | 10/1998 | Grandia et al. |
| 5,836,896 | A | 11/1998 | Rosenschein |
| 5,849,727 | A | 12/1998 | Porter et al. |
| 5,873,902 | A | 2/1999 | Sanghvi et al. |
| 5,879,314 | A | 3/1999 | Peterson et al. |
| 5,928,169 | A | 7/1999 | Schitzle et al. |
| 5,932,807 | A | 8/1999 | Mallart |
| 5,947,904 | A | 9/1999 | Hossack et al. |
| 6,001,069 | A | 12/1999 | Tachibana et al. |
| 6,007,499 | A | 12/1999 | Martin et al. |
| 6,022,309 | A | 2/2000 | Celliers et al. |
| 6,036,667 | A | 3/2000 | Manna et al. |
| 6,065,166 | A | 5/2000 | Sharrock et al. |
| 6,088,613 | A | 7/2000 | Unger |
| 6,093,883 | A | 7/2000 | Sanghvi et al. |
| 6,113,558 | A | 9/2000 | Rosenschein et al. |
| 6,126,607 | A | 10/2000 | Whitmore, III et al. |
| 6,128,958 | A | 10/2000 | Cain |
| 6,143,018 | A | 11/2000 | Beuthan et al. |
| 6,165,144 | A | 12/2000 | Talish et al. |
| 6,176,842 | B1 | 1/2001 | Tachibana et al. |
| 6,296,619 | B1 | 10/2001 | Brisken et al. |
| 6,308,585 | B1 | 10/2001 | Nilsson et al. |
| 6,308,710 | B1 | 10/2001 | Silva |

(56) References Cited

U.S. PATENT DOCUMENTS 6,309,355 B1 10/2001 Cain et al.
6,318,146 B1 11/2001 Madsen et al.
6,321,109 B2 11/2001 Ben-Haim et al.
6,338,566 B1 1/2002 Verdier
6,344,489 B1 2/2002 Spears
6,391,020 B1 5/2002 Kurtz et al.
6,413,216 B1 7/2002 Cain et al.
6,419,648 B1 7/2002 Vitek et al.
6,424,885 B1 * 7/2002 Niemeyer .............. A61B 34/77 600/109
6,470,204 B1 10/2002 Uzgiris et al.
6,488,639 B1 12/2002 Ribault et al.
6,490,469 B2 12/2002 Candy
6,500,141 B1 12/2002 Irion et al.
6,506,154 B1 1/2003 Ezion et al.
6,506,171 B1 1/2003 Vitek et al.
6,508,774 B1 1/2003 Acker et al.
6,511,428 B1 1/2003 Azuma et al.
6,511,444 B2 1/2003 Hynynen et al.
6,522,142 B1 2/2003 Freundlich
6,524,251 B2 2/2003 Rabiner et al.
6,536,553 B1 3/2003 Scanlon
6,543,272 B1 4/2003 Vitek
6,556,750 B2 4/2003 Constantino et al.
6,559,644 B2 5/2003 Froundlich et al.
6,576,220 B2 6/2003 Unger
6,599,288 B2 7/2003 Maguire et al.
6,607,498 B2 8/2003 Eshel
6,612,988 B2 9/2003 Maor et al.
6,613,004 B1 9/2003 Vitek et al.
6,613,005 B1 9/2003 Friedman et al.
6,626,854 B2 9/2003 Friedman et al.
6,626,855 B1 9/2003 Weng et al.
6,645,162 B2 11/2003 Friedman et al.
6,648,839 B2 11/2003 Manna et al.
6,666,833 B1 12/2003 Friedman et al.
6,685,640 B1 2/2004 Fry et al.
6,685,657 B2 2/2004 Jones
6,705,994 B2 3/2004 Vortman et al.
6,719,449 B1 4/2004 Laugham, Jr. et al.
6,719,694 B2 4/2004 Weng et al.
6,735,461 B2 5/2004 Vitek et al.
6,736,814 B2 5/2004 Manna et al.
6,750,463 B1 6/2004 Riley
6,770,031 B2 8/2004 Hynynen et al.
6,775,438 B1 8/2004 Gaedke et al.
6,788,977 B2 9/2004 Fenn et al.
6,790,180 B2 9/2004 Vitek
6,820,160 B1 11/2004 Allman
6,852,082 B2 2/2005 Strickberger et al.
6,869,439 B2 3/2005 White et al.
6,890,332 B2 5/2005 Truckal et al.
6,929,609 B2 8/2005 Asafusa
7,004,282 B2 2/2006 Manna et al.
7,059,168 B2 6/2006 Hibi et al.
7,128,711 B2 10/2006 Medan et al.
7,128,719 B2 10/2006 Rosenberg
7,175,596 B2 2/2007 Vitek et al.
7,175,599 B2 2/2007 Hynynen et al.
7,196,313 B2 3/2007 Quinones
7,223,239 B2 5/2007 Schulze et al.
7,258,674 B2 8/2007 Cribbs et al.
7,273,458 B2 9/2007 Prausnitz et al.
7,273,459 B2 9/2007 Desilets et al.
7,300,414 B1 11/2007 Holland et al.
7,311,679 B2 12/2007 Desilets et al.
7,331,951 B2 2/2008 Eshel et al.
7,341,569 B2 3/2008 Soltani et al.
7,347,855 B2 3/2008 Eshel et al.
7,358,226 B2 4/2008 Dayton et al.
7,359,640 B2 4/2008 Onde et al.
7,367,948 B2 5/2008 O'Donnell et al.
7,374,551 B2 5/2008 Liang et al.
7,377,900 B2 5/2008 Vitek et al.
7,429,249 B1 9/2008 Winder et al.
7,431,704 B2 10/2008 Babaev
7,442,168 B2 10/2008 Novak et al.
7,462,488 B2 12/2008 Madsen et al.
7,559,905 B2 7/2009 Kagosaki et al.
7,656,638 B2 2/2010 Laakso et al.
7,695,437 B2 4/2010 Quistgaard et al.
7,714,481 B2 5/2010 Sakai
7,771,359 B2 8/2010 Adam
7,967,763 B2 6/2011 Deem et al.
8,057,408 B2 11/2011 Cain et al.
8,295,912 B2 10/2012 Gertner
8,333,115 B1 12/2012 Garvey et al.
8,337,407 B2 12/2012 Quistgaard et al.
8,342,467 B2 1/2013 Stachowski et al.
8,376,970 B2 2/2013 Babaev
8,539,813 B2 9/2013 Cain et al.
8,568,339 B2 10/2013 Rybyanets
8,636,664 B2 1/2014 Brannan
8,715,187 B2 5/2014 Landberg Davis et al.
8,845,537 B2 9/2014 Tanaka et al.
8,932,239 B2 1/2015 Sokka et al.
9,028,434 B2 5/2015 Tanaka
9,049,783 B2 6/2015 Teofilovic
9,061,131 B2 6/2015 Jahnke et al.
9,144,694 B2 9/2015 Cain
9,220,476 B2 12/2015 Coussios et al.
9,228,730 B1 1/2016 Inbody
9,302,124 B2 4/2016 Konofagou et al.
9,457,201 B2 10/2016 Hoelscher et al.
9,526,923 B2 12/2016 Jahnke et al.
9,636,133 B2 5/2017 Hall et al.
9,642,634 B2 5/2017 Cain et al.
9,763,688 B2 9/2017 Stulen et al.
9,901,753 B2 2/2018 Cain et al.
9,943,708 B2 4/2018 Roberts et al.
10,022,107 B2 7/2018 Thornton et al.
10,046,179 B2 8/2018 Oskar-Kohler
10,046,181 B2 8/2018 Barthe et al.
10,058,352 B2 8/2018 Carvell et al.
10,071,266 B2 9/2018 Cain
10,130,828 B2 11/2018 Vortman et al.
10,219,815 B2 3/2019 Maxwell et al.
10,293,187 B2 5/2019 Cannata et al.
10,751,015 B2 8/2020 Anderson et al.
10,751,125 B2 8/2020 Levy et al.
10,765,892 B1 9/2020 Vitek et al.
10,772,646 B2 9/2020 Lu et al.
10,780,298 B2 9/2020 Cain et al.
10,791,991 B2 10/2020 Burkett et al.
10,799,209 B2 10/2020 Lahti et al.
10,806,421 B2 10/2020 Keller
10,820,813 B2 11/2020 Alpert
10,847,264 B2 11/2020 Mansker et al.
10,849,511 B2 12/2020 Tochterman et al.
10,869,603 B2 12/2020 Millett et al.
10,869,633 B2 12/2020 Burkett
10,869,648 B2 12/2020 Hubbard et al.
10,874,353 B2 12/2020 Assif
10,874,409 B2 12/2020 Matsubara et al.
10,878,586 B2 12/2020 Brokman et al.
10,888,232 B2 1/2021 Anderson et al.
10,893,808 B2 1/2021 Dorando
10,900,933 B2 1/2021 Prus et al.
10,905,394 B2 2/2021 Stigall et al.
10,912,463 B2 2/2021 Davies et al.
10,925,688 B2 2/2021 Millett et al.
10,927,003 B2 2/2021 Millett et al.
10,932,678 B2 3/2021 Burkett
10,939,826 B2 3/2021 Glynn et al.
10,942,022 B2 3/2021 Johansson et al.
10,973,419 B2 4/2021 Corl
10,993,618 B2 5/2021 Mansker et al.
10,993,628 B2 5/2021 Tochterman
10,993,694 B2 5/2021 Meyer et al.
11,000,185 B2 5/2021 Stigall et al.
11,006,840 B2 5/2021 Stigall
11,013,491 B2 5/2021 Rice et al.
11,020,087 B2 6/2021 Hoffman
11,020,089 B2 6/2021 Cort

(56) References Cited

U.S. PATENT DOCUMENTS 11,026,591 B2 6/2021 Burkett et al.
11,040,140 B2 6/2021 Unser et al.
11,058,399 B2 7/2021 Xu et al.
11,071,522 B2 7/2021 Hynynen et al.
11,103,731 B2 8/2021 Vortman et al.
11,112,473 B2 9/2021 Assif
11,119,552 B2 9/2021 Spencer et al.
11,120,896 B2 9/2021 Balignasay et al.
11,123,019 B2 9/2021 Merritt et al.
11,123,575 B2 9/2021 Vortman et al.
11,135,454 B2 10/2021 Xu et al.
11,141,063 B2 10/2021 Kemp et al.
11,141,131 B2 10/2021 Stigall et al.
11,160,513 B2 11/2021 Anderson et al.
11,205,507 B2 12/2021 Anderson et al.
11,219,748 B2 1/2022 Burkett et al.
11,224,349 B2 1/2022 Davies et al.
11,224,403 B2 1/2022 Corl
11,224,407 B2 1/2022 Wrolstad et al.
11,234,649 B2 2/2022 Matsubara et al.
11,246,533 B2 2/2022 Henderson et al.
11,246,565 B2 2/2022 Corl
11,253,225 B2 2/2022 Hancock et al.
11,260,160 B2 3/2022 Matsubara et al.
11,272,845 B2 3/2022 Cheline et al.
11,272,904 B2 3/2022 Vortman et al.
11,291,866 B2 4/2022 Levy et al.
11,298,030 B2 4/2022 Davies et al.
11,309,071 B2 4/2022 Anderson
11,311,271 B2 4/2022 Stigall et al.
11,324,410 B2 5/2022 Burkett
11,350,906 B2 6/2022 Castella et al.
11,350,954 B2 6/2022 De Cicco et al.
11,364,042 B2 6/2022 Maxwell et al.
11,369,346 B2 6/2022 De Cicco et al.
11,369,994 B2 6/2022 Greenberg et al.
11,395,638 B2 7/2022 Shin et al.
11,406,334 B2 8/2022 Merritt
11,406,355 B2 8/2022 Hoffman et al.
11,406,498 B2 8/2022 Stigall et al.
11,408,987 B2 8/2022 Vignon et al.
11,413,017 B2 8/2022 Stigall et al.
11,419,580 B2 8/2022 Stigall et al.
11,426,140 B2 8/2022 Sudol et al.
11,432,795 B2 9/2022 Merritt
11,432,900 B2 9/2022 Rakic et al.
11,446,000 B2 9/2022 Minas et al.
11,452,496 B2 9/2022 Minas et al.
11,452,506 B2 9/2022 Perez et al.
11,471,215 B2 10/2022 Stigall et al.
11,484,294 B2 11/2022 Hancock et al.
11,510,632 B2 11/2022 Begin et al.
11,517,291 B2 12/2022 Kantor et al.
11,520,874 B2 12/2022 Kennedy et al.
11,527,001 B2 12/2022 Brokman et al.
11,547,389 B2 1/2023 Shin et al.
11,553,889 B2 1/2023 Spencer et al.
11,554,386 B2 1/2023 Pernot et al.
11,559,207 B2 1/2023 Stigall et al.
11,567,153 B2 1/2023 Stormont et al.
11,576,649 B2 2/2023 Corl
11,576,652 B2 2/2023 De Cicco et al.
11,583,193 B2 2/2023 Groenland et al.
11,589,835 B2 2/2023 Stigall et al.
11,596,351 B2 3/2023 Nair
11,596,384 B2 3/2023 Nair et al.
11,596,387 B2 3/2023 Song
11,596,389 B2 3/2023 Nair
11,596,469 B2 3/2023 Nair
11,622,746 B2 4/2023 Minas et al.
11,638,576 B2 5/2023 Groenland et al.
11,647,989 B2 5/2023 Hope Simpson et al.
11,653,895 B2 5/2023 Stigall et al.
11,660,070 B2 5/2023 Stigall et al.
11,666,245 B2 6/2023 Rajguru et al.
11,666,307 B2 6/2023 Unser
11,672,433 B2 6/2023 Park et al.
11,672,552 B2 6/2023 Pasquino et al.
11,672,953 B2 6/2023 May
11,684,342 B2 6/2023 Groenland et al.
11,684,807 B2 6/2023 Vortman et al.
11,707,207 B2 7/2023 Stigall et al.
11,707,254 B2 7/2023 Di Tuillio et al.
11,733,881 B2 8/2023 Perez
11,737,728 B2 8/2023 Davies et al.
11,744,527 B2 9/2023 Scott et al.
11,744,547 B2 9/2023 Hynynen
11,759,169 B2 9/2023 Cori
11,759,174 B2 9/2023 Saroha et al.
11,766,237 B2 9/2023 Anderson
11,771,370 B2 10/2023 Hynynen
11,771,405 B2 10/2023 Rhodes
11,771,869 B2 10/2023 Cicco
11,806,167 B2 11/2023 Burkett
11,854,687 B2 12/2023 Keller
11,857,362 B2 1/2024 Wrolstad et al.
11,857,807 B2 1/2024 Levy et al.
11,864,918 B2 1/2024 Burkett et al.
11,872,412 B2 1/2024 Vortman et al.
11,879,973 B2 1/2024 Prus et al.
11,883,235 B2 1/2024 Stigall et al.
11,890,025 B2 2/2024 Stigall et al.
11,890,136 B2 2/2024 Stigall et al.
11,890,137 B2 2/2024 Jenkins et al.
11,950,954 B2 4/2024 Hyun et al.
11,963,822 B2 4/2024 Wrolstad
11,986,682 B2 5/2024 Prus et al.
11,992,366 B2 5/2024 Stigall et al.
12,017,013 B2 6/2024 Sasamine et al.
12,035,919 B2 7/2024 Unser
12,036,066 B2 7/2024 De Cicco et al.
12,053,194 B2 8/2024 Goertz et al.
12,082,970 B2 9/2024 Goodman
12,096,949 B2 9/2024 Fermi et al.
12,097,072 B2 9/2024 Stigall et al.
12,112,850 B2 10/2024 Kuo et al.
12,115,007 B2 10/2024 Merritt et al.
12,144,677 B2 11/2024 Corl
12,167,931 B2 12/2024 Corl
12,178,642 B2 12/2024 Rajguru et al.
12,178,643 B2 12/2024 Stigall et al.
12,186,130 B2 1/2025 Davies
12,220,259 B2 2/2025 Burkett et al.
12,232,907 B2 2/2025 Chao et al.
12,246,195 B2 3/2025 Levy et al.
12,257,461 B2 3/2025 Son et al.
12,263,035 B2 4/2025 Stigall et al.
12,402,802 B2 9/2025 Vitek et al.
12,440,188 B2 10/2025 Chao et al.
12,465,477 B2 11/2025 Pasquino et al.
2001/0039420 A1 11/2001 Burbank et al.
2001/0041163 A1 11/2001 Sugita
2002/0045890 A1 4/2002 Celliers et al.
2002/0078964 A1 6/2002 Kovac et al.
2002/0099356 A1 7/2002 Unger et al.
2002/0145091 A1 10/2002 Talish et al.
2003/0092982 A1 5/2003 Eppstein
2003/0112922 A1 6/2003 Burdette et al.
2003/0149352 A1 8/2003 Liang et al.
2003/0157025 A1 8/2003 Unger et al.
2003/0169591 A1 9/2003 Cochran
2003/0181833 A1 9/2003 Faragalla et al.
2003/0199857 A1 10/2003 Eizenhofer
2003/0221561 A1 12/2003 Milo
2003/0236539 A1 12/2003 Rabiner et al.
2004/0127815 A1 7/2004 Marchitto et al.
2004/0138563 A1 7/2004 Moehring et al.
2004/0162571 A1 8/2004 Rabiner et al.
2004/0164213 A1 8/2004 Stephan
2004/0236248 A1 11/2004 Svedman
2004/0243021 A1 12/2004 Murphy et al.
2004/0249509 A1 12/2004 Rogers et al.
2004/0260214 A1 12/2004 Echt et al.
2005/0011296 A1 1/2005 Koseki

(56) References Cited

U.S. PATENT DOCUMENTS

2005/0020945 A1 1/2005 Tosaya et al.
2005/0038339 A1 2/2005 Chauhan et al.
2005/0038361 A1 2/2005 Zhong et al.
2005/0152561 A1 7/2005 Spencer
2005/0154314 A1 7/2005 Quistgaard
2005/0154431 A1 7/2005 Quistgaard et al.
2005/0203399 A1 9/2005 Vaezy et al.
2005/0215901 A1 9/2005 Anderson et al.
2005/0234438 A1 10/2005 Mast et al.
2005/0283098 A1 12/2005 Conston et al.
2006/0058678 A1 3/2006 Vitek et al.
2006/0060991 A1 3/2006 Holsteyns et al.
2006/0074303 A1 4/2006 Chornenky et al.
2006/0089636 A1 4/2006 Christopherson et al.
2006/0173321 A1 8/2006 Kubota et al.
2006/0173387 A1 8/2006 Hansmann et al.
2006/0184166 A1 8/2006 Valle et al.
2006/0206028 A1 9/2006 Lee et al.
2006/0229659 A1 10/2006 Gifford et al.
2006/0241466 A1 10/2006 Ottoboni et al.
2006/0241523 A1 10/2006 Sinelnikov et al.
2006/0241533 A1 10/2006 Geller
2006/0264760 A1 11/2006 Liu et al.
2006/0293598 A1 12/2006 Fraser
2006/0293630 A1 12/2006 Manna et al.
2007/0010805 A1 1/2007 Fedewa et al.
2007/0016039 A1* 1/2007 Vortman .................. A61N 7/02 601/2
2007/0044562 A1 3/2007 Sarr
2007/0065420 A1 3/2007 Johnson
2007/0083120 A1 4/2007 Cain et al.
2007/0140413 A1 6/2007 Saracen
2007/0161902 A1 7/2007 Dan
2007/0167764 A1 7/2007 Hynynen
2007/0205785 A1 9/2007 Nilsson
2007/0219448 A1 9/2007 Seip et al.
2007/0239001 A1 10/2007 Mehl et al.
2007/0270683 A1 11/2007 Meloy
2008/0013593 A1 1/2008 Kawabata
2008/0033297 A1 2/2008 Sliwa
2008/0033417 A1* 2/2008 Nields ................ A61B 18/1815 606/41
2008/0051656 A1 2/2008 Vaezy et al.
2008/0055003 A1 3/2008 Unnikrishnan et al.
2008/0082026 A1 4/2008 Schmidt et al.
2008/0091125 A1 4/2008 Owen et al.
2008/0126665 A1 5/2008 Burr et al.
2008/0154132 A1 6/2008 Hall et al.
2008/0167555 A1 7/2008 Qian et al.
2008/0177180 A1 7/2008 Azhari et al.
2008/0194965 A1 8/2008 Sliwa et al.
2008/0214964 A1 9/2008 Chapelon et al.
2008/0262345 A1 10/2008 Fichtinger et al.
2008/0262486 A1 10/2008 Zvuloni et al.
2008/0283303 A1 11/2008 Cote
2008/0300485 A1 12/2008 Liu et al.
2008/0312561 A1 12/2008 Chauhan
2008/0319376 A1 12/2008 Wilcox et al.
2009/0012514 A1 1/2009 Moonen et al.
2009/0030339 A1 1/2009 Cheng et al.
2009/0036773 A1 2/2009 Lau et al.
2009/0112098 A1 4/2009 Vaezy et al.
2009/0171254 A1 7/2009 Kushculey et al.
2009/0198094 A1 8/2009 Fenster et al.
2009/0211587 A1 8/2009 Lawrentschuk
2009/0227874 A1 9/2009 Suri et al.
2009/0230822 A1 9/2009 Kushculey et al.
2009/0254008 A1 10/2009 Shields, Jr.
2009/0287083 A1 11/2009 Kushculey et al.
2009/0306502 A1 12/2009 Lacoste
2010/0011845 A1 1/2010 Laugharn et al.
2010/0042020 A1 2/2010 Ben-Ezra
2010/0056924 A1 3/2010 Powers
2010/0059264 A1 3/2010 Hasegawa et al.
2010/0069797 A1 3/2010 Cain et al.
2010/0125225 A1 5/2010 Gelbart et al.
2010/0152624 A1 6/2010 Tanis et al.
2010/0163694 A1 7/2010 Fadler et al.
2010/0204578 A1 8/2010 Schmidt et al.
2010/0261994 A1 10/2010 Davalos et al.
2010/0274136 A1 10/2010 Cerofolini
2010/0286519 A1 11/2010 Lee et al.
2010/0298744 A1 11/2010 Altshuler et al.
2010/0305432 A1 12/2010 Duhay et al.
2010/0317971 A1 12/2010 Fan et al.
2010/0318002 A1 12/2010 Prus et al.
2011/0072970 A1 3/2011 Slobodzian et al.
2011/0112400 A1 5/2011 Emery et al.
2011/0118600 A1* 5/2011 Gertner .................... A61N 7/02 601/2
2011/0118602 A1 5/2011 Weng et al.
2011/0144490 A1 6/2011 Davis et al.
2011/0144545 A1 6/2011 Fan et al.
2011/0172529 A1 7/2011 Gertner
2011/0178444 A1 7/2011 Slayton et al.
2011/0245671 A1 10/2011 Sato
2011/0251528 A1 10/2011 Canney et al.
2011/0257524 A1 10/2011 Gertner
2011/0257561 A1 10/2011 Gertner et al.
2011/0263967 A1 10/2011 Bailey et al.
2011/0270136 A1 11/2011 Vitek et al.
2011/0302719 A1 12/2011 Schwirian et al.
2011/0319765 A1 12/2011 Gertner
2011/0319927 A1 12/2011 Nita
2012/0029337 A1 2/2012 Aoyagi
2012/0029353 A1 2/2012 Slayton et al.
2012/0029393 A1 2/2012 Lee
2012/0059264 A1 3/2012 Hope Simpson et al.
2012/0059285 A1 3/2012 Soltani et al.
2012/0065492 A1 3/2012 Gertner et al.
2012/0065493 A1 3/2012 Gertner
2012/0065494 A1 3/2012 Gertner et al.
2012/0092724 A1 4/2012 Pettis
2012/0111339 A1 5/2012 Barthe et al.
2012/0130288 A1 5/2012 Holland et al.
2012/0136279 A1 5/2012 Tanaka et al.
2012/0158013 A1 6/2012 Stefanchik et al.
2012/0172720 A1 7/2012 Asami et al.
2012/0189998 A1 7/2012 Kruecker et al.
2012/0215157 A1 8/2012 Berryman et al.
2012/0232388 A1 9/2012 Curra et al.
2012/0259250 A1 10/2012 Sapozhnikov et al.
2012/0271167 A1 10/2012 Holland et al.
2012/0271223 A1 10/2012 Khanna
2012/0281902 A1 11/2012 Oikawa et al.
2013/0051178 A1 2/2013 Rybyanets
2013/0053691 A1 2/2013 Kawabata et al.
2013/0090579 A1 4/2013 Cain et al.
2013/0102932 A1 4/2013 Cain et al.
2013/0144165 A1 6/2013 Ebbini et al.
2013/0172739 A1 7/2013 Paladini
2013/0190623 A1 7/2013 Bertolina et al.
2013/0190661 A1 7/2013 Wing et al.
2013/0255426 A1 10/2013 Kassow et al.
2013/0303906 A1 11/2013 Cain et al.
2014/0030806 A1 1/2014 Dudley et al.
2014/0039358 A1 2/2014 Zhou et al.
2014/0046181 A1 2/2014 Benchimol et al.
2014/0058293 A1 2/2014 Hynynen et al.
2014/0058294 A1* 2/2014 Gross ..................... A61B 8/546 601/2
2014/0073995 A1 3/2014 Teofilovic et al.
2014/0074076 A1 3/2014 Gertner
2014/0088613 A1 3/2014 Seo et al.
2014/0100459 A1 4/2014 Xu et al.
2014/0112107 A1 4/2014 Guo et al.
2014/0128734 A1 5/2014 Genstler et al.
2014/0200489 A1 7/2014 Behar et al.
2014/0243664 A1 8/2014 El-Sayed et al.
2014/0316269 A1 10/2014 Zhang et al.
2014/0324034 A1 10/2014 Assaf et al.
2014/0330124 A1 11/2014 Carol
2014/0378832 A1 12/2014 Sanghvi et al.

(56) References Cited

U.S. PATENT DOCUMENTS

2014/0378964 A1* 12/2014 Pearson ............. A61B 18/1477 606/41
2015/0011875 A1 1/2015 Noordhoek et al.
2015/0063668 A1 3/2015 You et al.
2015/0073261 A1 3/2015 Kohler et al.
2015/0080926 A1 3/2015 Emery
2015/0148659 A1 5/2015 Vahala
2015/0151141 A1 6/2015 Arnal et al.
2015/0190121 A1 7/2015 Slayton et al.
2015/0190659 A1 7/2015 Kolher
2015/0196239 A1 7/2015 Meehan et al.
2015/0224347 A1 8/2015 Barthe et al.
2015/0257779 A1* 9/2015 Sinelnikov ............. A61N 7/022 606/28
2015/0258352 A1 9/2015 Lin et al.
2015/0265243 A1 9/2015 Kelly
2015/0273246 A1 10/2015 Darlington et al.
2015/0297177 A1 10/2015 Boctor et al.
2015/0359603 A1* 12/2015 Levy ........................ A61N 7/02 703/2
2016/0004933 A1 1/2016 Hu et al.
2016/0038665 A1 2/2016 Schaefer et al.
2016/0114194 A1 4/2016 Gertner
2016/0120572 A1 5/2016 Lee
2016/0135782 A1 5/2016 Chen et al.
2016/0151618 A1 6/2016 Powers et al.
2016/0184614 A1 6/2016 Matula et al.
2016/0206341 A1 7/2016 Slayton
2016/0206867 A1 7/2016 Hossack et al.
2016/0249859 A1 9/2016 Babkin et al.
2016/0287909 A1 10/2016 Maxwell et al.
2016/0303166 A1 10/2016 Katz et al.
2016/0331583 A1 11/2016 Geringer
2016/0331585 A1 11/2016 Kim
2016/0339273 A1 11/2016 Al Mayiah
2016/0345938 A1 12/2016 Tanter et al.
2016/0354087 A1* 12/2016 Noonan ............. A61B 17/1285
2016/0361574 A1 12/2016 Barthe et al.
2017/0000376 A1 1/2017 Partanen et al.
2017/0042521 A1 2/2017 Popovic et al.
2017/0049463 A1 2/2017 Popovic et al.
2017/0071515 A1 3/2017 Chevillet et al.
2017/0072227 A1 3/2017 Khokhlova et al.
2017/0072228 A1 3/2017 Wang et al.
2017/0079519 A1 3/2017 Sung et al.
2017/0100145 A1 4/2017 Khoklova et al.
2017/0120080 A1 5/2017 Phillips et al.
2017/0165046 A1 6/2017 Johnson et al.
2017/0183062 A1 6/2017 Lee
2017/0197099 A1 7/2017 Ruebel et al.
2017/0232277 A1 8/2017 Hall et al.
2017/0263846 A1 9/2017 Nakamura et al.
2017/0281983 A1 10/2017 Marquet et al.
2018/0000444 A1 1/2018 Dayton et al.
2018/0008787 A1 1/2018 Schriver et al.
2018/0028841 A1 2/2018 Konofagou et al.
2018/0064412 A1* 3/2018 Messas .................... A61B 8/06
2018/0161086 A1 6/2018 Davalos et al.
2018/0169444 A1 6/2018 Averkiou et al.
2018/0206816 A1 7/2018 Prus et al.
2018/0236271 A1 8/2018 Tanter et al.
2018/0317884 A1 11/2018 Chapelon et al.
2018/0374471 A1 12/2018 Dirksen et al.
2019/0000422 A1 1/2019 West et al.
2019/0023804 A1 1/2019 Onik et al.
2019/0082998 A1 3/2019 Nowroozi et al.
2019/0275353 A1 9/2019 Cannata et al.
2019/0282294 A1 9/2019 Davalos et al.
2019/0314045 A1 10/2019 Cunitz et al.
2019/0320904 A1 10/2019 Mei
2019/0323086 A1 10/2019 Leuthardt et al.
2019/0328500 A1 10/2019 Cichon et al.
2020/0010575 A1 1/2020 Hode et al.
2020/0055085 A1 2/2020 Taffler
2020/0078608 A1 3/2020 Maxwell et al.
2020/0107843 A1 4/2020 Goertz et al.
2020/0164231 A1 5/2020 Cannata et al.
2020/0182989 A1 6/2020 Freeman et al.
2020/0194117 A1 6/2020 Krieger et al.
2020/0253550 A1 8/2020 Nair
2020/0254285 A1 8/2020 Jang et al.
2020/0260964 A1 8/2020 Collins et al.
2020/0282239 A1 9/2020 Beder et al.
2020/0289080 A1 9/2020 Yang et al.
2020/0305842 A1 10/2020 Rosenzweig et al.
2020/0308785 A1 10/2020 Sennhauser
2020/0323515 A1 10/2020 Levy
2020/0330039 A1 10/2020 Burkett et al.
2020/0330075 A1 10/2020 O'Reilly et al.
2020/0346044 A1 11/2020 Woodcare et al.
2020/0346046 A1 11/2020 Cannata et al.
2020/0353293 A1 11/2020 Khokhlova et al.
2020/0367835 A1 11/2020 Anderson
2020/0375576 A1 12/2020 Moulton
2020/0405258 A1 12/2020 Dayton et al.
2020/0405259 A1 12/2020 Merritt
2021/0000541 A1 1/2021 Levy et al.
2021/0008394 A1 1/2021 Cain et al.
2021/0009936 A1 1/2021 Kamen et al.
2021/0022703 A1 1/2021 Nair
2021/0022714 A1 1/2021 Zagrodsky et al.
2021/0100527 A1 4/2021 Martin
2021/0108866 A1 4/2021 Lucht et al.
2021/0161398 A1 6/2021 Millett et al.
2021/0169515 A1 6/2021 Pahk et al.
2021/0170204 A1 6/2021 Vortman et al.
2021/0170205 A1 6/2021 Vortman et al.
2021/0187331 A1 6/2021 Zadicario et al.
2021/0196295 A1* 7/2021 Goudot ................ A61B 8/4461
2021/0220607 A1 7/2021 Sasamine et al.
2021/0252313 A1 8/2021 Xu et al.
2021/0353161 A1 11/2021 Merritt et al.
2021/0386451 A1 12/2021 Escudero et al.
2021/0401400 A1 12/2021 Sheehan et al.
2022/0008036 A1 1/2022 Gulsen et al.
2022/0043143 A1 2/2022 Prus et al.
2022/0079563 A1 3/2022 Kemp
2022/0087640 A1 3/2022 Minas et al.
2022/0110809 A1 4/2022 Grindstaff et al.
2022/0166462 A1 5/2022 Deurenberg et al.
2022/0168470 A1 6/2022 Ricotti et al.
2022/0196771 A1 6/2022 Zur et al.
2022/0202483 A1 6/2022 Gertner
2022/0203139 A1 6/2022 Shapira
2022/0219019 A1 7/2022 Xu et al.
2022/0233890 A1 7/2022 Hynynen et al.
2022/0257329 A1 8/2022 Stigall et al.
2022/0280233 A1 9/2022 Park et al.
2022/0296211 A1 9/2022 Saroha et al.
2022/0338750 A1 10/2022 Allen et al.
2022/0346756 A1 11/2022 Chen
2022/0395333 A1 12/2022 Merritt et al.
2022/0409858 A1 12/2022 Lin
2023/0000466 A1 1/2023 Levy et al.
2023/0000469 A1 1/2023 Prus et al.
2023/0008714 A1 1/2023 Rajguru et al.
2023/0012365 A1 1/2023 Alpert et al.
2023/0024998 A1 1/2023 Greenberg
2023/0037603 A1 2/2023 Pombo et al.
2023/0038543 A1 2/2023 Minas et al.
2023/0042834 A1 2/2023 Henderson et al.
2023/0045488 A1 2/2023 Rajguru et al.
2023/0048979 A1 2/2023 Lindenmoyer et al.
2023/0050732 A1 2/2023 Hancock et al.
2023/0100912 A1 3/2023 Amar et al.
2023/0310901 A1 10/2023 Cannata et al.
2023/0372025 A1 11/2023 Van der Zaag et al.
2023/0389891 A1 12/2023 Cohen et al.
2023/0398381 A1 12/2023 Vitek et al.
2024/0000422 A1 1/2024 Corl
2024/0000426 A1 1/2024 Davies et al.
2024/0023928 A1 1/2024 Di Tullio et al.
2024/0023930 A1 1/2024 Anderson
2024/0023941 A1 1/2024 Rhodes

(56) References Cited

U.S. PATENT DOCUMENTS

| | | | |
|---|---|---|---|
| 2024/0065632 | A1 | 2/2024 | Burkett |
| 2024/0138807 | A1 | 5/2024 | Minas |
| 2024/0139553 | A1 | 5/2024 | Miller et al. |
| 2024/0165666 | A1 | 5/2024 | Hynynen et al. |
| 2024/0188929 | A1 | 6/2024 | Minas et al. |
| 2024/0188931 | A1 | 6/2024 | Ossmann et al. |
| 2024/0189267 | A1 | 6/2024 | Bogott et al. |
| 2024/0189628 | A1 | 6/2024 | Grumbir et al. |
| 2024/0269491 | A1 | 8/2024 | Xu et al. |
| 2024/0285978 | A1 | 8/2024 | Xu et al. |
| 2024/0299092 | A1 | 9/2024 | Boinagrov et al. |
| 2024/0307708 | A1 | 9/2024 | Cannata et al. |
| 2024/0315713 | A1 | 9/2024 | Maxwell et al. |
| 2024/0316367 | A1 | 9/2024 | Cannata et al. |
| 2024/0341732 | A1 | 10/2024 | Hoffman et al. |
| 2024/0374242 | A1 | 11/2024 | Merritt et al. |

FOREIGN PATENT DOCUMENTS

| | | | |
|---|---|---|---|
| CA | 3073552 | A1 | 3/2019 |
| CA | 3101381 | A1 | 11/2019 |
| CA | 3055856 | A1 | 4/2020 |
| CA | 3153080 | A1 | 4/2021 |
| CA | 2910561 | C | 7/2021 |
| CA | 2908740 | C | 10/2021 |
| CA | 2980976 | C | 3/2023 |
| CA | 2840014 | C | 8/2023 |
| CN | 1669672 | A | 9/2005 |
| CN | 1732031 | A | 2/2006 |
| CN | 201197744 | Y | 2/2009 |
| CN | 102292123 | A | 12/2011 |
| CN | 102481164 | A | 5/2012 |
| CN | 102665585 | A | 9/2012 |
| CN | 103537016 | A | 1/2014 |
| CN | 103648361 | A | 3/2014 |
| CN | 103812477 | A | 5/2014 |
| CN | 104013444 | A | 9/2014 |
| CN | 104135938 | A | 11/2014 |
| CN | 104208822 | A | 12/2014 |
| CN | 106999076 | B | 8/2017 |
| CN | 109185113 | A | 1/2019 |
| CN | 109219415 | A | 1/2019 |
| CN | 109689160 | A | 4/2019 |
| CN | 208725992 | U | 4/2019 |
| CN | 111565642 | A | 8/2020 |
| CN | 111655337 | A | 9/2020 |
| CN | 111699022 | A | 9/2020 |
| CN | 111712300 | A | 9/2020 |
| CN | 111712301 | A | 9/2020 |
| CN | 106999053 | B | 10/2020 |
| CN | 107660137 | B | 10/2020 |
| CN | 111757769 | A | 10/2020 |
| CN | 112204412 | A | 1/2021 |
| CN | 112236195 | A | 1/2021 |
| CN | 106661535 | B | 3/2021 |
| CN | 112533673 | A | 3/2021 |
| CN | 112566694 | A | 3/2021 |
| CN | 106999054 | B | 5/2021 |
| CN | 106793997 | B | 6/2021 |
| CN | 107530049 | B | 6/2021 |
| CN | 112912011 | A | 6/2021 |
| CN | 112912012 | A | 6/2021 |
| CN | 112912013 | A | 6/2021 |
| CN | 112969413 | A | 6/2021 |
| CN | 112996445 | A | 6/2021 |
| CN | 113167877 | A | 7/2021 |
| CN | 113196080 | A | 7/2021 |
| CN | 109196369 | B | 8/2021 |
| CN | 109200484 | B | 8/2021 |
| CN | 113316419 | A | 8/2021 |
| CN | 113329788 | A | 8/2021 |
| CN | 2908740 | C | 10/2021 |
| CN | 109640830 | B | 10/2021 |
| CN | 113473917 | A | 10/2021 |
| CN | 113507946 | A | 10/2021 |
| CN | 113518588 | A | 10/2021 |
| CN | 108135565 | B | 11/2021 |
| CN | 113705586 | A | 11/2021 |
| CN | 110662575 | B | 12/2021 |
| CN | 113905666 | A | 1/2022 |
| CN | 114222536 | A | 3/2022 |
| CN | 114423362 | A | 4/2022 |
| CN | 108351394 | B | 5/2022 |
| CN | 110248606 | B | 6/2022 |
| CN | 115227992 | A | 10/2022 |
| CN | 109843181 | B | 11/2022 |
| CN | 115461000 | A | 12/2022 |
| CN | 109091768 | B | 3/2023 |
| CN | 115779285 | A | 3/2023 |
| CN | 115779287 | A | 3/2023 |
| CN | 115813438 | A | 3/2023 |
| CN | 111032157 | B | 4/2023 |
| CN | 110958858 | B | 5/2023 |
| CN | 116172611 | A | 5/2023 |
| CN | 111655337 | B | 6/2023 |
| CN | 109416908 | B | 7/2023 |
| CN | 107529989 | B | 8/2023 |
| CN | 111372522 | B | 8/2023 |
| CN | 116617589 | A | 8/2023 |
| CN | 112236195 | B | 9/2023 |
| CN | 113615098 | B | 9/2023 |
| CN | 114555247 | B | 9/2023 |
| CN | 109416907 | B | 10/2023 |
| CN | 111212606 | B | 3/2024 |
| CN | 113490459 | B | 5/2024 |
| CN | 112601498 | B | 9/2024 |
| CN | 113271866 | B | 10/2024 |
| CN | 112603273 | B | 12/2024 |
| CN | 112639754 | B | 12/2024 |
| CN | 119367006 | A | 1/2025 |
| CN | 112704620 | B | 2/2025 |
| CN | 110410498 | B | 3/2025 |
| CN | 112426634 | B | 3/2025 |
| CN | 111991712 | B | 9/2025 |
| CN | 112494106 | B | 10/2025 |
| DE | 3220751 | A1 | 12/1983 |
| DE | 3544628 | A1 | 6/1987 |
| DE | 3817094 | A1 | 11/1989 |
| DE | 4012760 | A1 | 5/1992 |
| DE | 602020055151 | T2 | 7/2025 |
| DE | 602020058523 | T2 | 9/2025 |
| DE | 602020059056 | T2 | 9/2025 |
| DE | 602017092008 | T2 | 10/2025 |
| EP | 0017382 | A1 | 10/1980 |
| EP | 0320303 | A2 | 6/1989 |
| EP | 0332871 | A2 | 9/1989 |
| EP | 0384831 | A2 | 8/1990 |
| EP | 0619156 | A1 | 10/1994 |
| EP | 0755653 | A1 | 1/1997 |
| EP | 1374785 | A1 | 1/2004 |
| EP | 1504713 | A1 | 2/2005 |
| EP | 1566201 | A2 | 8/2005 |
| EP | 2397188 | A1 | 12/2011 |
| EP | 2934308 | B1 | 10/2015 |
| EP | 2934309 | B1 | 10/2015 |
| EP | 3097180 | B1 | 11/2016 |
| EP | 2759003 | B1 | 8/2020 |
| EP | 3558457 | A4 | 8/2020 |
| EP | 3700629 | A1 | 9/2020 |
| EP | 3218829 | B1 | 10/2020 |
| EP | 3229688 | B1 | 10/2020 |
| EP | 3723857 | A1 | 10/2020 |
| EP | 2887989 | B1 | 2/2021 |
| EP | 3777689 | A1 | 2/2021 |
| EP | 2938253 | B1 | 3/2021 |
| EP | 3076864 | B1 | 3/2021 |
| EP | 2802276 | B1 | 4/2021 |
| EP | 2809221 | B1 | 4/2021 |
| EP | 3801761 | A1 | 4/2021 |
| EP | 3801762 | A2 | 4/2021 |
| EP | 3801763 | A1 | 4/2021 |
| EP | 2967369 | B1 | 5/2021 |
| EP | 2967488 | B1 | 6/2021 |
| EP | 3184048 | B1 | 6/2021 |

(56) References Cited

FOREIGN PATENT DOCUMENTS

| | | | |
|---|---|---|---|
| EP | 2967370 | B1 | 9/2021 |
| EP | 3482390 | B1 | 9/2021 |
| EP | 3870067 | A1 | 9/2021 |
| EP | 3870069 | A1 | 9/2021 |
| EP | 3876843 | A1 | 9/2021 |
| EP | 2931130 | B1 | 10/2021 |
| EP | 2934304 | B1 | 10/2021 |
| EP | 3887843 | A1 | 10/2021 |
| EP | 3888534 | A1 | 10/2021 |
| EP | 3895604 | A1 | 10/2021 |
| EP | 3897391 | A1 | 10/2021 |
| EP | 3229672 | B1 | 11/2021 |
| EP | 3902603 | A1 | 11/2021 |
| EP | 3903672 | A1 | 11/2021 |
| EP | 2964096 | B1 | 12/2021 |
| EP | 3930776 | A1 | 1/2022 |
| EP | 3545829 | B1 | 3/2022 |
| EP | 3959530 | A2 | 3/2022 |
| EP | 3060129 | B1 | 4/2022 |
| EP | 3986296 | A1 | 4/2022 |
| EP | 3988167 | A1 | 4/2022 |
| EP | 2914166 | B1 | 5/2022 |
| EP | 3229674 | B1 | 5/2022 |
| EP | 2779907 | B1 | 6/2022 |
| EP | 3102098 | B1 | 6/2022 |
| EP | 4017382 | A1 | 6/2022 |
| EP | 2965263 | B1 | 7/2022 |
| EP | 2726152 | B1 | 8/2022 |
| EP | 4041387 | A1 | 8/2022 |
| EP | 4042936 | A1 | 8/2022 |
| EP | 3298959 | B2 | 9/2022 |
| EP | 2931131 | B1 | 11/2022 |
| EP | 2938268 | B1 | 11/2022 |
| EP | 3581103 | B1 | 11/2022 |
| EP | 4087492 | A1 | 11/2022 |
| EP | 4093470 | A1 | 11/2022 |
| EP | 3091905 | B1 | 12/2022 |
| EP | 4098203 | A1 | 12/2022 |
| EP | 2950737 | B1 | 1/2023 |
| EP | 3057496 | B1 | 1/2023 |
| EP | 2869804 | B1 | 2/2023 |
| EP | 2938265 | B1 | 2/2023 |
| EP | 3024403 | B1 | 3/2023 |
| EP | 4151156 | A1 | 3/2023 |
| EP | 2938271 | B1 | 4/2023 |
| EP | 4179995 | A2 | 5/2023 |
| EP | 3171764 | B1 | 6/2023 |
| EP | 2931132 | B1 | 7/2023 |
| EP | 3229695 | B1 | 7/2023 |
| EP | 4226864 | A1 | 8/2023 |
| EP | 4230121 | A2 | 8/2023 |
| EP | 4230146 | A1 | 8/2023 |
| EP | 4233972 | A2 | 8/2023 |
| EP | 2866733 | B1 | 9/2023 |
| EP | 3870069 | B1 | 9/2023 |
| EP | 3484371 | B1 | 10/2023 |
| EP | 3658037 | B1 | 10/2023 |
| EP | 3685874 | B1 | 10/2023 |
| EP | 3870070 | B1 | 10/2023 |
| EP | 2938255 | B1 | 11/2023 |
| EP | 3229906 | B1 | 11/2023 |
| EP | 3764914 | B1 | 11/2023 |
| EP | 3903672 | B1 | 11/2023 |
| EP | 4272654 | A2 | 11/2023 |
| EP | 4275609 | A2 | 11/2023 |
| EP | 3316804 | B1 | 12/2023 |
| EP | 3519109 | B1 | 12/2023 |
| EP | 3166479 | B1 | 1/2024 |
| EP | 3537984 | B1 | 1/2024 |
| EP | 3908195 | B1 | 2/2024 |
| EP | 3182920 | B1 | 3/2024 |
| EP | 3174643 | B1 | 4/2024 |
| EP | 3814917 | B1 | 4/2024 |
| EP | 3681419 | B1 | 5/2024 |
| EP | 4368118 | A2 | 5/2024 |
| EP | 2804525 | B1 | 6/2024 |
| EP | 3324836 | B1 | 9/2024 |
| EP | 3624732 | B1 | 11/2024 |
| EP | 3190958 | B1 | 2/2025 |
| EP | 4282471 | B1 | 3/2025 |
| EP | 4041463 | B1 | 8/2025 |
| EP | 3986296 | B1 | 9/2025 |
| ES | 2774069 | T3 | 7/2020 |
| ES | 2819552 | T3 | 4/2021 |
| ES | 2829822 | T3 | 6/2021 |
| ES | 2998435 | T3 | 2/2025 |
| ES | 3005837 | T3 | 3/2025 |
| GB | 2099582 | A | 12/1982 |
| HK | 1245715 | B | 1/2021 |
| IL | 254768 | A | 5/2021 |
| IL | 261285 | B | 2/2022 |
| IN | 202117039853 | A | 12/2021 |
| IN | 387413 | B | 1/2022 |
| IN | 445766 | B | 8/2023 |
| JP | 60-80779 | A | 5/1985 |
| JP | 61-196718 | A | 8/1986 |
| JP | 02-215451 | A | 8/1990 |
| JP | H0422351 | A | 1/1992 |
| JP | 06-197907 | A | 7/1994 |
| JP | 07-504339 | A | 5/1995 |
| JP | 08-84740 | A | 4/1996 |
| JP | 06-304178 | A | 5/1996 |
| JP | 08-131454 | A | 5/1996 |
| JP | 09-55571 | A | 2/1997 |
| JP | 10-512477 | A | 12/1998 |
| JP | 2000300559 | A | 10/2000 |
| JP | 2003510159 | A | 3/2003 |
| JP | 2004505660 | A | 2/2004 |
| JP | 2004249106 | A | 9/2004 |
| JP | 2005167058 | A | 6/2005 |
| JP | 2006511265 | A | 4/2006 |
| JP | 2007144225 | A | 6/2007 |
| JP | 2007520307 | A | 7/2007 |
| JP | 2010019554 | A | 1/2010 |
| JP | 2010029650 | A | 2/2010 |
| JP | 2010204068 | A | 9/2010 |
| JP | 2013538097 | A | 10/2013 |
| JP | 2004512502 | A | 4/2014 |
| JP | 2015002983 | A | 1/2015 |
| JP | 2015519970 | A | 7/2015 |
| JP | 2016508808 | A | 3/2016 |
| JP | 2017/506542 | A | 3/2017 |
| JP | 2017506538 | A | 3/2017 |
| JP | 2019051295 | A | 4/2019 |
| JP | 2020525167 | A | 8/2020 |
| JP | 2020525168 | A | 8/2020 |
| JP | 2020525169 | A | 8/2020 |
| JP | 6785554 | B2 | 10/2020 |
| JP | 6789944 | B2 | 11/2020 |
| JP | 2020534077 | A | 11/2020 |
| JP | 2020195788 | A | 12/2020 |
| JP | 2020535895 | A | 12/2020 |
| JP | 6832958 | B2 | 2/2021 |
| JP | 6835719 | B2 | 2/2021 |
| JP | 6838057 | B2 | 3/2021 |
| JP | 6849592 | B2 | 3/2021 |
| JP | 2021510104 | A | 4/2021 |
| JP | 6896719 | B2 | 6/2021 |
| JP | 6934933 | B2 | 9/2021 |
| JP | 6951560 | B2 | 10/2021 |
| JP | 6979633 | B2 | 12/2021 |
| JP | 6980696 | B2 | 12/2021 |
| JP | 7012726 | B2 | 1/2022 |
| JP | 2022500092 | A | 1/2022 |
| JP | 2022500093 | A | 1/2022 |
| JP | 2022501080 | A | 1/2022 |
| JP | 2022504159 | A | 1/2022 |
| JP | 2022509389 | A | 1/2022 |
| JP | 2022509391 | A | 1/2022 |
| JP | 2022509392 | A | 1/2022 |
| JP | 2022509393 | A | 1/2022 |
| JP | 2022509395 | A | 1/2022 |
| JP | 2022509401 | A | 1/2022 |
| JP | 2022509453 | A | 1/2022 |

(56) References Cited

FOREIGN PATENT DOCUMENTS

| | | | |
|---|---|---|---|
| JP | 2022510217 | A | 1/2022 |
| JP | 7019679 | B2 | 2/2022 |
| JP | 7026118 | B2 | 2/2022 |
| JP | 2022514272 | A | 2/2022 |
| JP | 2022515488 | A | 2/2022 |
| JP | 2022516078 | A | 2/2022 |
| JP | 7053500 | B2 | 4/2022 |
| JP | 2022526104 | A | 5/2022 |
| JP | 2022527043 | A | 5/2022 |
| JP | 2022095785 | A | 6/2022 |
| JP | 7171645 | B2 | 11/2022 |
| JP | 7171663 | B2 | 11/2022 |
| JP | 7175640 | B2 | 11/2022 |
| JP | 2022546288 | A | 11/2022 |
| JP | 7187715 | B2 | 12/2022 |
| JP | 2022551875 | A | 12/2022 |
| JP | 2022552229 | A | 12/2022 |
| JP | 7201819 | B2 | 1/2023 |
| JP | 7232204 | B2 | 3/2023 |
| JP | 7239466 | B2 | 3/2023 |
| JP | 7265525 | B2 | 4/2023 |
| JP | 2023071859 | A | 5/2023 |
| JP | 7299992 | B2 | 6/2023 |
| JP | 7302936 | B2 | 7/2023 |
| JP | 7304344 | B2 | 7/2023 |
| JP | 7321162 | B2 | 8/2023 |
| JP | 7325430 | B2 | 8/2023 |
| JP | 7340594 | B2 | 9/2023 |
| JP | 7346293 | B2 | 9/2023 |
| JP | 7352561 | B2 | 9/2023 |
| JP | 7358391 | B2 | 10/2023 |
| JP | 7359765 | B2 | 10/2023 |
| JP | 7370386 | B2 | 10/2023 |
| JP | 2023162327 | A | 11/2023 |
| JP | 2024010135 | A | 1/2024 |
| JP | 2024020483 | A | 2/2024 |
| JP | 7479288 | B2 | 5/2024 |
| JP | 7479351 | B2 | 5/2024 |
| JP | 7485383 | B2 | 5/2024 |
| JP | 7530561 | B2 | 8/2024 |
| JP | 7542708 | B2 | 8/2024 |
| JP | 2024161427 | A | 11/2024 |
| JP | 7612816 | B2 | 1/2025 |
| JP | 7641600 | B2 | 3/2025 |
| KR | 102574559 | B1 | 9/2023 |
| KR | 102854907 | B1 | 9/2025 |
| RU | 2589649 | C1 | 7/2016 |
| WO | WO94/06355 | A1 | 3/1994 |
| WO | WO02/32506 | A1 | 4/2002 |
| WO | WO2005/018469 | A1 | 3/2005 |
| WO | WO2008/051484 | A2 | 5/2008 |
| WO | WO2011/040054 | A1 | 7/2011 |
| WO | WO2011/092683 | A1 | 8/2011 |
| WO | WO2011/154654 | A2 | 12/2011 |
| WO | WO2014/008594 | A1 | 1/2014 |
| WO | WO2014/071386 | A1 | 5/2014 |
| WO | WO2015/000953 | A1 | 1/2015 |
| WO | WO2015/031532 | A1 | 3/2015 |
| WO | WO2015/153909 | A2 | 10/2015 |
| WO | WO2016/099279 | A1 | 6/2016 |
| WO | WO2018/149671 | A1 | 8/2018 |
| WO | WO2018/208189 | A1 | 11/2018 |
| WO | WO2019/081329 | A1 | 5/2019 |
| WO | WO2019/122941 | A1 | 6/2019 |
| WO | WO2019/148154 | A1 | 8/2019 |
| WO | WO2020/074615 | A1 | 4/2020 |
| WO | WO2020/087049 | A1 | 4/2020 |
| WO | WO2020/112688 | A1 | 6/2020 |
| WO | WO2020/217098 | A2 | 10/2020 |
| WO | WO2020/237382 | A1 | 12/2020 |
| WO | WO2020/245660 | A1 | 12/2020 |
| WO | WO2021/014221 | A1 | 1/2021 |
| WO | WO2021/032887 | A1 | 2/2021 |
| WO | WO2021/069216 | A1 | 4/2021 |
| WO | WO2021/069971 | A1 | 4/2021 |
| WO | WO2021/089810 | A1 | 5/2021 |
| WO | WO2021/105358 | A1 | 6/2021 |
| WO | WO2021/115958 | A1 | 6/2021 |
| WO | WO2021/116763 | A1 | 6/2021 |
| WO | WO2021/122253 | A1 | 6/2021 |
| WO | WO2021/123905 | A2 | 6/2021 |
| WO | WO2021/123906 | A1 | 6/2021 |
| WO | WO2021/140042 | A1 | 7/2021 |
| WO | WO2021/142090 | A1 | 7/2021 |
| WO | WO2021/170510 | A1 | 9/2021 |
| WO | WO2021/175626 | A1 | 9/2021 |
| WO | WO2021/176275 | A1 | 9/2021 |
| WO | WO2021/178961 | A1 | 9/2021 |
| WO | WO2021/180501 | A1 | 9/2021 |
| WO | WO2021/180550 | A1 | 9/2021 |
| WO | WO2021/213927 | A1 | 10/2021 |
| WO | WO2021/249936 | A1 | 12/2021 |
| WO | WO2021/258007 | A1 | 12/2021 |
| WO | WO2022/013266 | A1 | 1/2022 |
| WO | WO2022/040493 | A1 | 2/2022 |
| WO | WO2022/047193 | A1 | 3/2022 |
| WO | WO2022/056394 | A1 | 3/2022 |
| WO | WO2022/069254 | A1 | 4/2022 |
| WO | WO2022/069303 | A2 | 4/2022 |
| WO | WO2022/069327 | A2 | 4/2022 |
| WO | WO2022/078744 | A1 | 4/2022 |
| WO | WO2022/097138 | A1 | 5/2022 |
| WO | WO2022/106891 | A1 | 5/2022 |

OTHER PUBLICATIONS

Rakic et al.; U.S. Appl. No. 17/929,951 entitled "Articulating arm limiter for cavitational ultrasound therapy system," filed Sep. 6, 2022.

Gateau et al.; Transcranial ultrasonic therapy based on time reversal of acoustically induced cavitation bubble signature. IEEE Transactions on Biomedical Engineering: 57(1); pp. 134-144; Sep. 18, 2009.

Kim et al.; Development of a wearable robotic positioning system for noninvasive transcranial focused ultrasound stimulation. IEEE/ASME Transactions on Mechatronics; 21(5); pp. 2284-2293; Jun. 13, 2016.

Cannata et al.; U.S. Appl. No. 18/464,877 entitled "Histotripsy systems and methods," filed Sep. 11, 2023.

Cannata et al.; U.S. Appl. No. 18/464,721 entitled "Histotripsy systems and methods," filed Sep. 11, 2023.

Xu et al.; U.S. Appl. No. 18/478,342 entitled "Systems and methods for histotripsy immunosensitization," filed Sep. 29, 2023.

Duryea et al.; U.S. Appl. No. 18/497,856 entitled "Histotripsy systems and methods," filed Oct. 31, 2023.

Duryea et al.; U.S. Appl. No. 18/498,966 entitled "Histotripsy systems and methods," filed Oct. 31, 2023.

Duryea et al.; U.S. Appl. No. 18/498,979 entitled "Histotripsy systems and methods," filed Oct. 31, 2023.

Cain et al.; U.S. Appl. No. 18/485,904 entitled "Histotripsy using very short ultrasound pulses," filed Oct. 12, 2023.

Xu et al.; U.S. Appl. No. 18/555,683 entitled "Design and fabrication of therapeutic ultrasound transducer with arbitrarily shaped, densely packing, removable modular elements," filed Oct. 16, 2023.

Cannata et al.; U.S. Appl. No. 18/311,045 entitled "Histotripsy systems and methods," filed May 2, 2023.

Cannata et al.; U.S. Appl. No. 18/311,050 entitled "Histotripsy systems and methods," filed May 2, 2023.

Maxwell et al.; U.S. Appl. No. 18/329,459 entitled "Histotripsy for thrombolysis," filed Jun. 5, 2023.

Hall et al.; U.S. Appl. No. 18/043,251 entitled "Ultrasound transducer with transmit-receive capability for histotripsy," filed Feb. 27, 2023.

Xu et al.; U.S. Appl. No. 18/0744,867 entitled "Transcranial mr-guided histotripsy systems and methods," filed Mar. 10, 2023.

Stopek et al.; U.S. Appl. No. 18/002,204 entitled "Histotripsy acoustic and patient coupling systems and methods," filed Dec. 16, 2022.

(56) References Cited

OTHER PUBLICATIONS

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
Appel et al.; Stereoscopic highspeed recording of bubble filaments; Ultrasonics Sonochemistry; vol. 11(1); pp. 39-42; Jan. 2004.
Arani et al.; Transurethral prostate magnetic resonance elestography; prospective imaging requirements; Magn. Reson. Med.; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging: 13(1); pp. 57-63; Jan. 2001.
Atchley et al.; Thresholds for cavitation produced in water by pulsed ultrasound; Ultrasonics.; vol. 26(5); pp. 280-285; Sep. 1988.
Avago Technologies; ACNV2601 High Insulation Voltage 10 MBd Digital Opotcoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
Avtech; AVR-8 Data sheet; May 23, 2004; 3 pages; retrieved from the internet (http//www.avtechpulse.com).
Bak; Rapid protytyping or rapid production? 3D printing processes move industry towards the latter; Assembly Automation; 23(4); pp. 340-345; Dec. 1, 2003.
Billson et al.; Rapid prototyping technologies for ultrasonic beam focussing in NDE; IEEE International Ultrasonic Symposium Proceedings; pp. 2472-2474; Oct. 2011.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vasc Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Dovedi et al.; Acquired Resistance to Fractionated Radiotherapy Can Be Overcome by Concurrent PD-LI Blockade; Cancer Research; 74(19); pp. 5458-5468; Oct. 1, 2014.
Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Haller et al.; Determination of acoustic cavitation probabilities and thresholds using a single focusing transducer to induce and detect acoustic cavitation events: I. Method and terminology; Ultrasound in Medicine & Biology; 44(2); pp. 377-396; Feb. 1, 2018.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue) 1993.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Lin et al.; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).

(56) References Cited

OTHER PUBLICATIONS

Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; p. 220-223; Sep. 20, 2009.
Maxwell et al.; The role of compressional pressure in the formation of dense bubble clouds in histotripsy; 2009 IEEE International Ultrasonics Symposium; pp. 81-84; Sep. 20, 2009.
Miller et al.; A review of in vitro bioeffects of inertial ultrasonic cavitation from a mechanistic perspective; Ultrasound in Medicine and Biology; vol. 22; pp. 1131-1154; (the year of publication is sufficiently earlier than the effective U.S. filing date and any foreign priority date so that the particular month of publication is not in issue) 1996.
Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.
Miller et al.; Real-time elastography-based monitoring of histotripsy tissue fractionation using color doppler; Ultrasonics Symposium (IUS); 2012 IEEE International; 8 pages; Oct. 7-10, 2012.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Qu et al.; Non-thermal histotripsy tumor ablation promotes abscopal immune responses that enhance cancer immunotherapy; Journal for immunotherapy of cancer; 8(1); Jan. 15, 2020.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.
Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group, Non-invasive Ultrasonic Tissue Fraction for Treatment of Benign Disease and Cancer—"Histotripsy". University research [online]. Biomedical Engineering Department, University of Michigan. Jul. 2011 [retrieved on Jan. 28, 2014] from: (http://web.archive.org/web/20110720091822/http://www.histotripsy.umich.edu/index.html>.entiredocument) Jul. 2011.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.
Van Kervel et al.; A calculation scheme for the optimum design of ultrasonic transducers; Ultrasonics, vol. 21, pp. 134-140, May 1983.

(56) References Cited

OTHER PUBLICATIONS

Wang et al.; Quantitative ultrasound backscatter for pulsed cavitational ultrasound therapy—histotripsy; Ultrasonics, Ferroelectrics and Frequency Control, IEEE Transactions on, vol. 56, pp. 995-1005, May 2009.
Wikipedia; Medical ultrasound; 15 pages; retrieved from the internet (https://en.wikipedia.org/w/index.php?title=Medical_utrasound&oldid=515340960) on Jan. 12, 2018.
Wu et al.; Mechanism and dynamics of hydrodynamic-acoustic cavitation (HAC); Ultrasonics sonochemistry; vol. 49., pp. 89-96; Dec. 1, 2018.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.
Xu et al.; Controlled ultrasound tissue erosion: the role of dynamic interaction between insonation and microbubble activity; Journal of the Acoustical Society of America; vol. 117(1); pp. 424-435; Jan. 2005.
Xu et al.; Controlled ultrasound tissue erosion; IEEE Transaction on Ultrasonics, Ferroelectrics, and Frequency Control; vol. 51 (6); pp. 726-736; Jun. 2004.
Xu et al.; Effects of acoustic parameters on bubble cloud dynamics in ultrasound tissue erosion (histotripsy); Journal of the Acoustical Society of America; vol. 122(1); pp. 229-236; Jul. 2007.
Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31(12); pp. 1673-1682; Dec. 2005.
Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.
Yan et al.; A review of rapid prototyping technologies and systems; Computer-Aided Design, vol. 28, pp. 307-318, Apr. 1996.
Zhang et al.; A fast tissue stiffness-dependent elastography for HIFU-induced lesions inspection; Ultrasonics; 51(8); pp. 857-869; Dec. 2011.
Zheng et al.; An acoustic backscatter-based method for localization of lesions induced by high-intensity focused ultrasound; Ultrasound Med Biol; 36(4); pp. 610-622; Apr. 2010.
Maxwell et al.; U.S. Appl. No. 17/838,085 entitled "Histotripsy for thrombolysis," filed Jun. 10, 2022.
Kisting et al.; Imaging for targeting, monitoring, and assessment after histotripsy: a non-invasive, non-thermal therapy for cancer; Blood Vessels; vol. 10; pp. 15-21; Mar. 2023.
Woodacre et al.; A low-cost miniature histotripsy transducer for precision tissue ablation. IEEE transactions on ultrasonics, ferroelectrics, and frequency control; 65(11); pp. 2131-2140; Nov. 1, 2018.
Bader et al.; For whom the bubble grows: physical principles of bubble nucleation and dynamics in histotripsy ultrasound therapy; Ultrasound in medicine & biology; 45(5); pp. 1056-1080, May 1, 2019.
Cain et al.; Concentric-ring and sector-vortex phased-array applicators for ultrasound hyperthermia; IEEE Transactions on Microwave Theory and Techniques; 34(5); pp. 542-551; May 1986.
Hynynen et al.; Feasibility of using ultrasound phased arrays for MRI monitored noninvasive surgery; IEEE transactions on ultrasonics, ferroelectrics, and frequency control; 43(6); pp. 1043-1053; Nov. 1996.
International Society for Magnetic Resonance in Medicine (ISMRM); No. 105; XP040714022;I Jul. 24, 2020.
Hoogenboom et al.; Mechanical high-intensity focused ultrasound destruction of soft tissue: working mechanisms and physiologic effects; Ultrasound in medicine & biology; 41(6); pp. 1500-1517; Jun. 1, 2015.
Sukovich et al.; Real-time transcranial histotripsy treatment localization and mapping using acoustic cavitation emission feedback; IEEE transactions on ultrasonics, ferroelectrics, and frequency control, 67(6); pp. 1178-1791; Jan. 17, 2020.
Cannata et al.; U.S. Appl. No. 18/630,758 entitled "Histotripsy systems and methods," filed Apr. 9, 2024.
Cannata et al.; U.S. Appl. No. 18/642,529 entitled "Histotripsy systems and associated methods including user interfaces and workflows for treatment planning and therapy," filed Apr. 22, 2024.
Stopek.; U.S. Appl. No. 18/761,937 entitled "Minimally invasive histotripsy systems and methods," filed Jul. 2, 2024.
Shaffer et al.; U.S. Appl. No. 18/832,708 entitled "Histotripsy systems and methods," filed Jul. 24, 2024.
Rosnitskiy et al.; Method for designing multielement fully populated random phased arrays for ultrasound surgery applications. IEEE transactions on ultrasonics, ferroelectrics, and frequency control; 65(4); pp. 630-637; Jan. 31, 2018.

* cited by examiner

SYSTEMS AND METHODS FOR ROBOTICALLY-ASSISTED HISTOTRIPSY TARGETING BASED ON MRI/CT SCANS TAKEN PRIOR TO TREATMENT

CROSS REFERENCE TO RELATED APPLICATIONS

This application claims the benefit of priority of U.S. Provisional Patent Application No. 62/958,209, filed Jan. 7, 2020, titled "Systems and Methods for Robotically-Assisted Histotripsy Targeting Based on MRI/CT Scans Taken Prior to Treatment", incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

STATEMENT AS TO FEDERALLY SPONSORED RESEARCH

This invention was made with Government support under NS108042 awarded by the National Institutes of Health. The Government has certain rights in the invention.

FIELD

The present disclosure details novel high intensity therapeutic ultrasound (HITU) systems configured to produce acoustic cavitation, methods, devices and procedures for the minimally and non-invasive treatment of healthy, diseased and/or injured tissue. The acoustic cavitation systems and methods described herein, also referred to Histotripsy, may include transducers, drive electronics, positioning robotics, imaging systems, and integrated treatment planning and control software to provide comprehensive treatment and therapy for soft tissues in a patient.

BACKGROUND

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, and high-intensity focused ultrasound (HIFU), Histotripsy relies on the mechanical action of cavitation for tissue destruction.

SUMMARY OF THE DISCLOSURE

A method of surgical navigation is provided, comprising receiving, in a surgical navigation system, a first image of a target tissue volume, obtaining, with the surgical navigation system, a second image of the target tissue volume, co-registering, in the surgical navigation system, the first image with the second image to identify boundary coordinates of the target tissue volume in the first image, identifying, with the surgical navigation system, focal coordinates of a focus of a histotripsy therapy transducer, determining, in the surgical navigation system, movement coordinates that will place the histotripsy therapy transducer focus within the boundary coordinates of the target tissue volume in the first image, and moving the histotripsy therapy transducer focus based on the movement coordinates to place the histotripsy therapy transducer focus within the target tissue volume.

In some implementations, the moving step further comprises moving the histotripsy therapy transducer with a robotic positioning system. Alternatively, the moving step further comprises electronically steering the histotripsy therapy transducer focus.

In one implementation, the first image comprises a high-resolution image from an advanced diagnostic medical imaging system, such as a high-resolution MRI image, a high-resolution CT image, a cone beam CT image, or an augmented fluoroscopy image.

In other implementations, the second image comprises an ultrasound image, a photograph, or an optical image.

In some implementations, the co-registering step further comprises identifying a fiducial region in both the first image and the second image and using the fiducial region to correlate a coordinate system of the first image with a coordinate system of the second image.

In another implementation, identifying focal coordinates further comprises placing fiducial markers on the histotripsy therapy transducer and identifying the fiducial markers with the surgical navigation system.

In one implementation, the method further includes defining a treatment margin of the target tissue volume, calculating 3D grid locations to cover the target tissue volume and the treatment margin, and displaying the 3D grid locations over the first or second image. In another example, the treatment margin comprises a positive treatment margin that extends beyond the target tissue volume. In some implementations, the treatment margin comprises a negative treatment margin that extends within the target tissue volume.

In many implementations, the method further comprises applying histotripsy therapy to the target tissue volume.

In some implementations, the method further includes imaging the histotripsy therapy and peri-procedurally updating co-registration between the first image and the second image.

In one implementation, the method further comprises producing a histotripsy treatment map, and overlaying the histotripsy treatment map on the first or second image in real time.

In some examples, the robotic positioning system can move the histotripsy therapy transducer with 3 degrees of freedom. In other examples, the robotic positioning system can move the histotripsy therapy transducer with 6 degrees of freedom.

In one embodiment, the moving step further comprises a combination of electronically steering the histotripsy therapy transducer focus and moving the histotripsy therapy transducer with a robotic positioning system.

In various implementations, the target tissue volume can comprise a tumor, a clot, an organ, or a brain hemorrhage.

Another method of surgical navigation is provided, comprising inserting an acoustic detector into tissue within or near a target tissue volume, localizing a position of the target tissue volume relative to a focus of a histotripsy therapy transducer with the acoustic detector, and determining movement coordinates required to place the histotripsy therapy transducer focus within the target tissue volume.

In some embodiments, the method further comprises applying histotripsy therapy with the histotripsy therapy transducer.

In one implementation, the inserting step further comprises inserting a catheter into tissue within or near the target tissue volume, wherein the catheter includes the acoustic detector. In another implementation, the inserting step further comprises inserting a needle into tissue within or near the target tissue volume, wherein the needle includes the acoustic detector.

A method of surgical navigation is provided, comprising inserting a fiducial marker into tissue within or near a target tissue volume, localizing a position of the target tissue volume relative to a focus of a histotripsy therapy transducer with the fiducial marker, and determining movement coordinates required to place the histotripsy therapy transducer focus within the target tissue volume.

In some embodiments, the method further comprises applying histotripsy therapy with the histotripsy therapy transducer.

A therapy system is provided, comprising a first imaging system, a surgical navigation system including a second imaging system, a robotic positioning arm, a histotripsy therapy transducer coupled to the robotic positioning arm, and an electronic controller operatively coupled to the first imaging system, the surgical navigation system, the second imaging system, the robotic positioning arm, and the histotripsy therapy transducer, the electronic controller being configured to co-register a first image of the target tissue volume from the first imaging system with a second imaging of the target tissue volume from the second imaging system to identify boundary coordinates of the target tissue volume, the electronic controller being further configured to determine movement coordinates of the robotic positioning arm requires to place a focus of the histotripsy therapy transducer within the target tissue volume.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The system, methods and devices of the disclosure may be used for the minimally or non-invasive acoustic cavitation and treatment of healthy, diseased and/or injured tissue, including in extracorporeal, percutaneous, endoscopic, laparoscopic, and/or as integrated into a robotically-enabled medical system and procedures. As will be described below, the acoustic cavitation system may include various sub-systems, including a Cart, Therapy, Integrated Imaging, Robotics, Coupling and Software. The system also may comprise various Other Components, Ancillaries and Accessories, including but not limited to computers, cables and connectors, networking devices, power supplies, displays, drawers/storage, doors, wheels, and various simulation and training tools, etc. All systems, methods and means creating/controlling/delivering histotripsy are considered to be a part of this disclosure, including new related inventions disclosed herein.

Figure 1A:
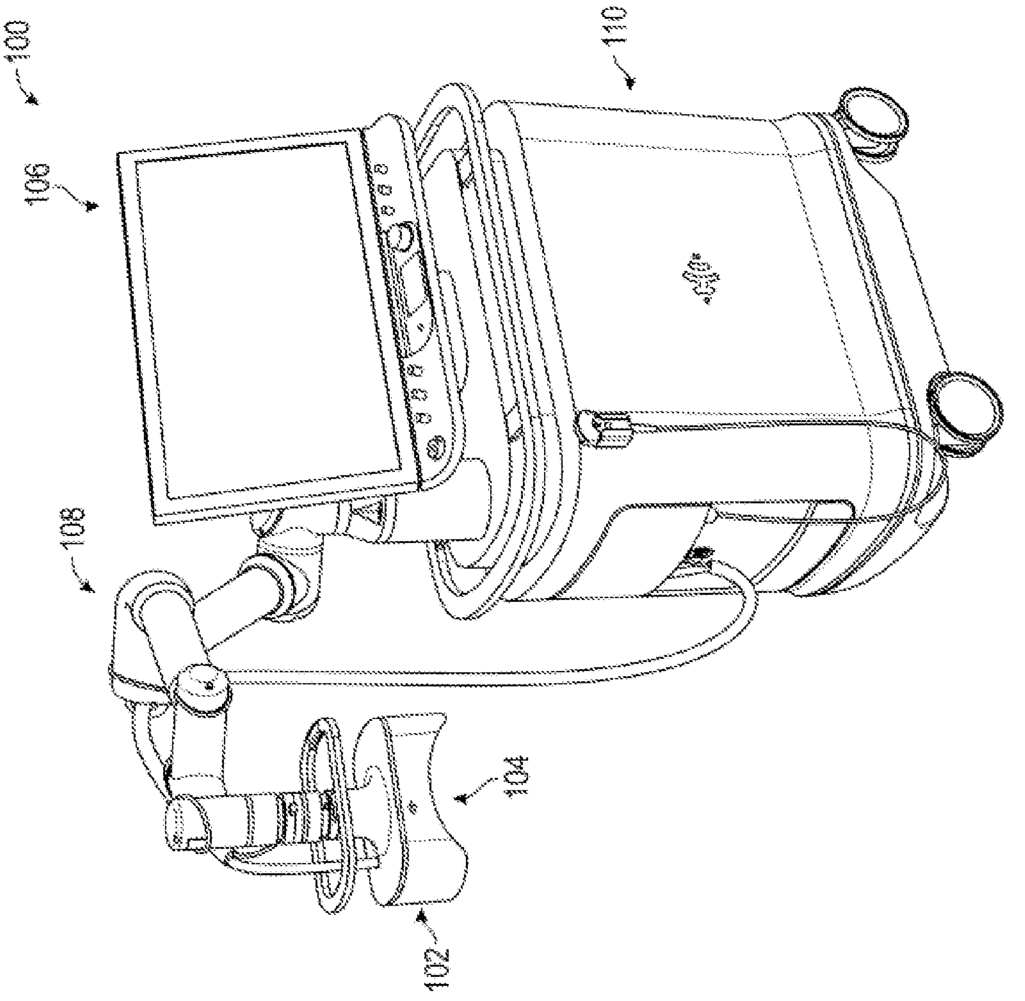
FIGS. 1A-1B illustrate an ultrasound imaging and therapy system.

FIG. 1A generally illustrates histotripsy system 100 according to the present disclosure, comprising a therapy transducer 102, an imaging system 104, a display and control panel 106, a robotic positioning arm 108, and a cart 110. The system can further include an ultrasound coupling interface and a source of coupling medium, not shown.

Figure 1B:
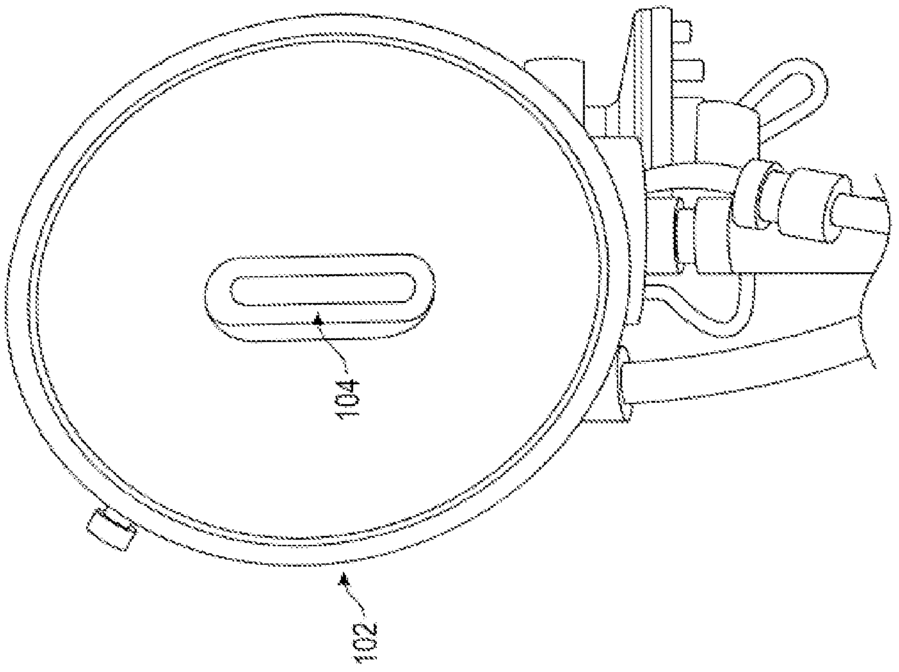

FIG. 1B is a bottom view of the therapy transducer 102 and the imaging system 104. As shown, the imaging system can be positioned in the center of the therapy transducer. However, other embodiments can include the imaging system positioned in other locations within the therapy transducer, or even directly integrated into the therapy transducer. In some embodiments, the imaging system is configured to produce real-time imaging at a focal point of the therapy transducer.

The histotripsy system may comprise one or more of various sub-systems, including a Therapy sub-system that can create, apply, focus and deliver acoustic cavitation/histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided work-flows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with imaging (e.g., CT, cone beam CT and/or MRI scanning). In other embodiments, it may be arranged for use in an operating room and a sterile environment, or in a robotically enabled operating room, and used alone, or as part of a surgical robotics procedure wherein a surgical robot conducts specific tasks before, during or after use of the system and delivery of acoustic cavitation/histotripsy. As such and depending on the procedure environment based on the aforementioned embodiments, the cart may be positioned to provide sufficient work-space and access to various anatomical locations on the patient (e.g., torso, abdomen, flank, head and neck, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, augmented fluoroscopy, optical, ultrasound, and image fusion and or image flow, of one or more modalities, to support the procedures and/or environments of use, including physical/mechanical interoperability (e.g., compatible within cone beam CT work-space for collecting imaging data pre, peri and/or post histotripsy).

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, “bubble cloud”, capable of the targeted fractionation and destruction of tissue. Histotripsy is capable of creating controlled tissue erosion when directed at a tissue interface, including tissue/fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses with a 1-2 cycles of high amplitude negative/tensile phase pressure exceeding the intrinsic threshold to generate cavitation in the medium (e.g., ~24-28 MPa for water-based soft tissue), 2) Shock-Scattering Histotripsy: Delivers typically pulses 3-20 cycles in duration. The shockwave (positive/compressive phase) scattered from an initial individual microbubble generated forms inverted shockwave, which constructively interfere with the incoming negative/tensile phase to form high amplitude negative/rarefactional phase exceeding the intrinsic threshold. In this way, a cluster of cavitation microbubbles is generated. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) tissue to the focal zone (treatment zone and site). It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the “shock scattering mechanism”.

This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHz) can be applied together with a high-frequency "probe" pulse (typically <2 cycles and having a frequency greater than 2 MHz, or ranging between 2 MHz and 10 MHz) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P− level for a region of interest (ROI), while the high-frequency pulse, which provides more precision, can pin-point a targeted location within the ROI and raise the peak negative pressure P− above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Therapy Components

The Therapy sub-system may work with other sub-systems to create, optimize, deliver, visualize, monitor and control acoustic cavitation, also referred to herein and in following as "histotripsy", and its derivatives of, including boiling histotripsy and other thermal high frequency ultrasound approaches. It is noted that the disclosed inventions may also further benefit other acoustic therapies that do not comprise a cavitation, mechanical or histotripsy component. The therapy sub-system can include, among other features, an ultrasound therapy transducer and a pulse generator system configured to deliver ultrasound pulses into tissue.

In order to create and deliver histotripsy and derivatives of histotripsy, the therapy sub-system may also comprise components, including but not limited to, one or more function generators, amplifiers, therapy transducers and power supplies.

The therapy transducer can comprise a single element or multiple elements configured to be excited with high amplitude electric pulses (>1000V or any other voltage that can cause harm to living organisms). The amplitude necessary to drive the therapy transducers for Histotripsy vary depending on the design of the transducer and the materials used (e.g., solid or polymer/piezoelectric composite including ceramic or single crystal) and the transducer center frequency which is directly proportional to the thickness of the piezo-electric material. Transducers therefore operating at a high frequency require lower voltage to produce a given surface pressure than is required by low frequency therapy transducers. In some embodiments, the transducer elements are formed using a piezoelectric-polymer composite material or a solid piezoelectric material. Further, the piezoelectric material can be of polycrystalline/ceramic or single crystalline formulation. In some embodiments the transducer elements can be formed using silicon using MEMs technology, including CMUT and PMUT designs.

In some embodiments, the function generator may comprise a field programmable gate array (FPGA) or other suitable function generator. The FPGA may be configured with parameters disclosed previously herein, including but not limited to frequency, pulse repetition frequency, bursts, burst numbers, where bursts may comprise pulses, numbers of pulses, length of pulses, pulse period, delays, burst repetition frequency or period, where sets of bursts may comprise a parameter set, where loop sets may comprise various parameter sets, with or without delays, or varied delays, where multiple loop sets may be repeated and/or new loop sets introduced, of varied time delay and independently controlled, and of various combinations and permutations of such, overall and throughout.

In some embodiments, the generator or amplifier may be configured to be a universal single-cycle or multi-cycle pulse generator, and to support driving via Class D or inductive driving, as well as across all envisioned clinical applications, use environments, also discussed in part later in this disclosure. In other embodiments, the class D or inductive current driver may be configured to comprise transformer and/or auto-transformer driving circuits to further provide step up/down components, and in some cases, to preferably allow a step up in the amplitude. They may also comprise specific protective features, to further support the system, and provide capability to protect other parts of the system (e.g., therapy transducer and/or amplifier circuit components) and/or the user, from various hazards, including but not limited to, electrical safety hazards, which may potentially lead to use environment, system and therapy system, and user harms, damage or issues.

Disclosed generators may allow and support the ability of the system to select, vary and control various parameters (through enabled software tools), including, but not limited to those previously disclosed, as well as the ability to start/stop therapy, set and read voltage level, pulse and/or burst repetition frequency, number of cycles, duty ratio, channel enabled and delay, etc., modulate pulse amplitude on a fast time-scale independent of a high voltage supply, and/or other service, diagnostic or treatment features.

In some embodiments, the Therapy sub-system and/or components of, such as the amplifier, may comprise further integrated computer processing capability and may be networked, connected, accessed, and/or be removable/portable, modular, and/or exchangeable between systems, and/or driven/commanded from/by other systems, or in various combinations. Other systems may include other acoustic cavitation/histotripsy, HIFU, HITU, radiation therapy, radiofrequency, microwave, and cryoablation systems, navigation and localization systems, laparoscopic, single incision/single port, endoscopic and non-invasive surgical robots, laparoscopic or surgical towers comprising other energy-based or vision systems, surgical system racks or booms, imaging carts, etc.

In some embodiments, one or more amplifiers may comprise a Class D amplifier and related drive circuitry including matching network components. Depending on the transducer element electric impedance and choice of the matching network components (e.g., an LC circuit made of an inductor L1 in series and the capacitor C1 in parallel), the combined impedance can be aggressively set low in order to have high amplitude electric waveform necessary to drive the transducer element. The maximum amplitude that Class D amplifiers is dependent on the circuit components used, including the driving MOSFET/IGBT transistors, matching network components or inductor, and transformer or autotransformer, and of which may be typically in the low kV (e.g., 1-3 kV) range.

Therapy transducer element(s) are excited with an electrical waveform with an amplitude (voltage) to produce a pressure output sufficient for Histotripsy therapy. The excitation electric field can be defined as the necessary waveform voltage per thickness of the piezoelectric element. For example, because a piezoelectric element operating at 1 MHz transducer is half the thickness of an equivalent 500 kHz element, it will require half the voltage to achieve the same electric field and surface pressure.

Integrated Imaging

The disclosed system may comprise various imaging modalities to allow users to visualize, monitor and collect/use feedback of the patient's anatomy, related regions of interest and treatment/procedure sites, as well as surrounding and intervening tissues to assess, plan and conduct procedures, and adjust treatment parameters as needed. Imaging modalities may comprise various ultrasound, x-ray, CT, MRI, PET, fluoroscopy, optical, contrast or agent enhanced versions, and/or various combinations of. It is further disclosed that various image processing and characterization technologies may also be utilized to afford enhanced visualization and user decision making. These may be selected or commanded manually by the user or in an automated fashion by the system. The system may be configured to allow side by side, toggling, overlays, 3D reconstruction, segmentation, registration, multi-modal image fusion, image flow, and/or any methodology affording the user to identify, define and inform various aspects of using imaging during the procedure, as displayed in the various system user interfaces and displays. Examples may include locating, displaying and characterizing regions of interest, organ systems, potential treatment sites within, with on and/or surrounding organs or tissues, identifying critical structures such as ducts, vessels, nerves, ureters, fissures, capsules, tumors, tissue trauma/injury/disease, other organs, connective tissues, etc., and/or in context to one another, of one or more (e.g., tumor draining lymphatics or vasculature; or tumor proximity to organ capsule or underlying other organ), as unlimited examples.

Systems may be configured to include onboard integrated imaging hardware, software, sensors, probes and wetware, and/or may be configured to communicate and interface with external imaging and image processing systems. The aforementioned components may be also integrated into the system's Therapy sub-system components wherein probes, imaging arrays, or the like, and electrically, mechanically or electromechanically integrated into therapy transducers. This may afford, in part, the ability to have geometrically aligned imaging and therapy, with the therapy directly within the field of view, and in some cases in line, with imaging. In some embodiments, this integration may comprise a fixed orientation of the imaging capability (e.g., imaging probe) in context to the therapy transducer. In other embodiments, the imaging solution may be able to move or adjust its position, including modifying angle, extension (e.g., distance from therapy transducer or patient), rotation (e.g., imaging plane in example of an ultrasound probe) and/or other parameters, including moving/adjusting dynamically while actively imaging. The imaging component or probe may be encoded so its orientation and position relative to another aspect of the system, such as the therapy transducer, and/or robotically-enabled positioning component may be determined.

In one embodiment, the system may comprise onboard ultrasound, further configured to allow users to visualize, monitor and receive feedback for procedure sites through the system displays and software, including allowing ultrasound imaging and characterization (and various forms of), ultrasound guided planning and ultrasound guided treatment, all in real-time. The system may be configured to allow users to manually, semi-automated or in fully automated means image the patient (e.g., by hand or using a robotically-enabled imager).

In some embodiments, imaging feedback and monitoring can include monitoring changes in: backscatter from bubble clouds; speckle reduction in backscatter; backscatter speckle statistics; mechanical properties of tissue (i.e., elastography); tissue perfusion (i.e., ultrasound contrast); shear wave propagation; acoustic emissions, electrical impedance tomography, and/or various combinations of, including as displayed or integrated with other forms of imaging (e.g., CT or MRI).

In some embodiments, imaging including feedback and monitoring from backscatter from bubble clouds, may be used as a method to determine immediately if the histotripsy process has been initiated, is being properly maintained, or even if it has been extinguished. For example, this method enables continuously monitored in real time drug delivery, tissue erosion, and the like. The method also can provide feedback permitting the histotripsy process to be initiated at a higher intensity and maintained at a much lower intensity. For example, backscatter feedback can be monitored by any transducer or ultrasonic imager. By measuring feedback for the therapy transducer, an accessory transducer can send out interrogation pulses or be configured to passively detect cavitation. Moreover, the nature of the feedback received can be used to adjust acoustic parameters (and associated system parameters) to optimize the drug delivery and/or tissue erosion process.

In some embodiments, imaging including feedback and monitoring from backscatter, and speckle reduction, may be configured in the system.

For systems comprising feedback and monitoring via backscattering, and as means of background, as tissue is progressively mechanically subdivided, in other words homogenized, disrupted, or eroded tissue, this process results in changes in the size and distribution of acoustic scatter. At some point in the process, the scattering particle size and density is reduced to levels where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound. After some treatment time, the speckle reduction results in a dark area in the therapy volume. Since the amount of speckle reduction is related to the amount of tissue subdivision, it can be related to the size of the remaining tissue fragments. When this size is reduced to sub-cellular levels, no cells are assumed to have survived. So, treatment can proceed until a desired speckle reduction level has been reached. Speckle is easily seen and evaluated on standard ultrasound imaging systems. Specialized transducers and systems, including those disclosed herein, may also be used to evaluate the backscatter changes.

Further, systems comprising feedback and monitoring via speckle, and as means of background, an image may persist from frame to frame and change very little as long as the scatter distribution does not change and there is no movement of the imaged object. However, long before the scatters are reduced enough in size to cause speckle reduction, they may be changed sufficiently to be detected by signal processing and other means. This family of techniques can operate as detectors of speckle statistics changes. For example, the size and position of one or more speckles in an image will begin to decorrelate before observable speckle reduction occurs. Speckle decorrelation, after appropriate motion compensation, can be a sensitive measure of the mechanical disruption of the tissues, and thus a measure of therapeutic efficacy. This feedback and monitoring technique may permit early observation of changes resulting from the acoustic cavitation/histotripsy process and can identify changes in tissue before substantial or complete tissue effect (e.g., erosion occurs). In one embodiment, this method may be used to monitor the acoustic cavitation/histotripsy process for enhanced drug delivery where treatment sites/tissue is temporally disrupted, and tissue damage/erosion is not desired. In other embodiments, this may comprise speckle decorrelation by movement of scatters in an increasingly fluidized therapy volume. For example, in the case where partial or complete tissue erosion is desired.

For systems comprising feedback and monitoring via elastography, and as means of background, as treatment sites/tissue are further subdivided per an acoustic cavitation/histotripsy effect (homogenized, disrupted, or eroded), its mechanical properties change from a soft but interconnected solid to a viscous fluid or paste with few long-range interactions. These changes in mechanical properties can be measured by various imaging modalities including MRI and ultrasound imaging systems. For example, an ultrasound pulse can be used to produce a force (i.e., a radiation force) on a localized volume of tissue. The tissue response (displacements, strains, and velocities) can change significantly during histotripsy treatment allowing the state of tissue disruption to be determined by imaging or other quantitative means.

Systems may also comprise feedback and monitoring via shear wave propagation changes. As means of background, the subdivision of tissues makes the tissue more fluid and less solid and fluid systems generally do not propagate shear waves. Thus, the extent of tissue fluidization provides opportunities for feedback and monitoring of the histotripsy process. For example, ultrasound and MRI imaging systems can be used to observe the propagation of shear waves. The extinction of such waves in a treated volume is used as a measure of tissue destruction or disruption. In one system embodiment, the system and supporting sub-systems may be used to generate and measure the interacting shear waves. For example, two adjacent ultrasound foci might perturb tissue by pushing it in certain ways. If adjacent foci are in a fluid, no shear waves propagate to interact with each other. If the tissue is not fluidized, the interaction would be detected with external means, for example, by a difference frequency only detected when two shear waves interact nonlinearly, with their disappearance correlated to tissue damage. As such, the system may be configured to use this modality to enhance feedback and monitoring of the acoustic cavitation/histotripsy procedure.

For systems comprising feedback and monitoring via acoustic emission, and as means of background, as a tissue volume is subdivided, its effect on acoustic cavitation/histotripsy (e.g., the bubble cloud here) is changed. For example, bubbles may grow larger and have a different lifetime and collapse changing characteristics in intact versus fluidized tissue. Bubbles may also move and interact after tissue is subdivided producing larger bubbles or cooperative interaction among bubbles, all of which can result in changes in acoustic emission. These emissions can be heard during treatment and they change during treatment. Analysis of these changes, and their correlation to therapeutic efficacy, enables monitoring of the progress of therapy, and may be configured as a feature of the system.

For systems comprising feedback and monitoring via electrical impedance tomography, and as means of background, an impedance map of a therapy site can be produced based upon the spatial electrical characteristics throughout the therapy site. Imaging of the conductivity or permittivity of the therapy site of a patient can be inferred from taking skin surface electrical measurements. Conducting electrodes are attached to a patient's skin and small alternating currents are applied to some or all of the electrodes. One or more known currents are injected into the surface and the voltage is measured at a number of points using the electrodes. The process can be repeated for different configurations of applied current. The resolution of the resultant image can be adjusted by changing the number of electrodes employed. A measure of the electrical properties of the therapy site within the skin surface can be obtained from the impedance map, and changes in and location of the acoustic cavitation/histotripsy (e.g., bubble cloud, specifically) and histotripsy process can be monitored using this as configured in the system and supporting sub-systems.

The user may be allowed to further select, annotate, mark, highlight, and/or contour, various regions of interest or treatment sites, and defined treatment targets (on the image(s)), of which may be used to command and direct the system where to image, test and/or treat, through the system software and user interfaces and displays. In some arrangements, the user may use a manual ultrasound probe (e.g., diagnostic hand-held probe) to conduct the procedure. In another arrangement, the system may use a robot and/or electromechanical positioning system to conduct the procedure, as directed and/or automated by the system, or conversely, the system can enable combinations of manual and automated uses.

The system may further include the ability to conduct image registration, including imaging and image data set registration to allow navigation and localization of the system to the patient, including the treatment site (e.g., tumor, critical structure, bony anatomy, anatomy and identifying features of, etc.). In one embodiment, the system allows the user to image and identify a region of interest, for example the liver, using integrated ultrasound, and to select and mark a tumor (or surrogate marker of) comprised within the liver through/displayed in the system software, and wherein said system registers the image data to a coordinate system defined by the system, that further allows the system's Therapy and Robotics sub-systems to deliver synchronized acoustic cavitation/histotripsy to said marked tumor. The system may comprise the ability to register various image sets, including those previously disclosed, to one another, as well as to afford navigation and localization (e.g., of a therapy transducer to a CT or MRI/ultrasound fusion image with the therapy transducer and Robotics sub-system tracking to said image).

The system may also comprise the ability to work in a variety of interventional, endoscopic and surgical environments, including alone and with other systems (surgical/laparoscopic towers, vision systems, endoscope systems and towers, ultrasound enabled endoscopic ultrasound (flexible and rigid), percutaneous/endoscopic/laparoscopic and minimally invasive navigation systems (e.g., optical, electromagnetic, shape-sensing, ultrasound-enabled, etc.), of also which may work with, or comprise various optical imaging capabilities (e.g., fiber and or digital). The disclosed system may be configured to work with these systems, in some embodiments working alongside them in concert, or in other embodiments where all or some of the system may be integrated into the above systems/platforms (e.g., acoustic cavitation/histotripsy-enabled endoscope system or laparoscopic surgical robot). In many of these environments, a therapy transducer may be utilized at or around the time of use, for example, of an optically guided endoscope/bronchoscope, or as another example, at the time a laparoscopic robot (e.g., Intuitive Da Vinci* Xi system) is viewing/manipulating a tissue/treatment site. Further, these embodiments and examples may include where said other systems/platforms are used to deliver (locally) fluid to enable the creation of a man-made acoustic window, where on under normal circumstances may not exist (e.g., fluidizing a segment or lobe of the lung in preparation for acoustic cavitation/histotripsy via non-invasive transthoracic treatment (e.g., transducer externally placed on/around patient). Systems disclosed herein may also comprise all or some of their sub-system hardware packaged within the other system cart/console/systems described here (e.g., acoustic cavitation/histotripsy system and/or sub-systems integrated and operated from said navigation or laparoscopic system).

The system may also be configured, through various aforementioned parameters and other parameters, to display real-time visualization of a bubble cloud in a spatial-temporal manner, including the resulting tissue effect peri/post-treatment from tissue/bubble cloud interaction, wherein the system can dynamically image and visualize, and display, the bubble cloud, and any changes to it (e.g., decreasing or increasing echogenicity), which may include intensity, shape, size, location, morphology, persistence, etc. These features may allow users to continuously track and follow the treatment in real-time in one integrated procedure and interface/system, and confirm treatment safety and efficacy on the fly (versus other interventional or surgical modalities, which either require multiple procedures to achieve the same, or where the treatment effect is not visible in real-time (e.g., radiation therapy), or where it is not possible to achieve such (e.g., real-time visualization of local tissue during thermal ablation), and/or where the other procedure further require invasive approaches (e.g., incisions or punctures) and iterative imaging in a scanner between procedure steps (e.g., CT or MRI scanning). The above disclosed systems, sub-systems, components, modalities, features and work-flows/methods of use may be implemented in an unlimited fashion through enabling hardware, software, user interfaces and use environments, and future improvements, enhancements and inventions in this area are considered as included in the scope of this disclosure, as well as any of the resulting data and means of using said data for analytics, artificial intelligence or digital health applications and systems.

Robotics

They system may comprise various Robotic sub-systems and components, including but not limited to, one or more robotic arms and controllers, which may further work with other sub-systems or components of the system to deliver and monitor acoustic cavitation/histotripsy. As previously discussed herein, robotic arms and control systems may be integrated into one or more Cart configurations.

For example, one system embodiment may comprise a Cart with an integrated robotic arm and control system, and Therapy, Integrated Imaging and Software, where the robotic arm and other listed sub-systems are controlled by the user through the form factor of a single bedside Cart.

In other embodiments, the Robotic sub-system may be configured in one or more separate Carts, that may be a driven in a master/slave configuration from a separate master or Cart, wherein the robotically-enabled Cart is positioned bed/patient-side, and the Master is at a distance from said Cart.

Disclosed robotic arms may be comprised of a plurality of joints, segments, and degrees of freedom and may also include various integrated sensor types and encoders, implemented for various use and safety features. Sensing technologies and data may comprise, as an example, vision, potentiometers, position/localization, kinematics, force, torque, speed, acceleration, dynamic loading, and/or others. In some cases, sensors may be used for users to direct robot commands (e.g., hand gesture the robot into a preferred set up position, or to dock home). Additional details on robotic arms can be found in US Patent Pub. No. 2013/0255426 to Kassow et al. which is disclosed herein by reference in its entirety.

The robotic arm receives control signals and commands from the robotic control system, which may be housed in a Cart. The system may be configured to provide various functionalities, including but not limited to, position, tracking, patterns, triggering, and events/actions.

Position may be configured to comprise fixed positions, pallet positions, time-controlled positions, distance-controlled positions, variable-time controlled positions, variable-distance controlled positions.

Tracking may be configured to comprise time-controlled tracking and/or distance-controlled tracking.

The patterns of movement may be configured to comprise intermediate positions or waypoints, as well as sequence of positions, through a defined path in space.

Triggers may be configured to comprise distance measuring means, time, and/or various sensor means including those disclosed herein, and not limited to, visual/imaging-based, force, torque, localization, energy/power feedback and/or others.

Events/actions may be configured to comprise various examples, including proximity-based (approaching/departing a target object), activation or de-activation of various end-effectors (e.g., therapy transducers), starting/stopping/pausing sequences of said events, triggering or switching between triggers of events/actions, initiating patterns of movement and changing/toggling between patterns of movement, and/or time-based and temporal over the defined work and time-space.

In one embodiment, the system comprises a three degree of freedom robotic positioning system, enabled to allow the user (through the software of the system and related user interfaces), to micro-position a therapy transducer through X, Y, and Z coordinate system, and where gross macro-positioning of the transducer (e.g., aligning the transducer on the patient's body) is completed manually. In some embodiments, the robot may comprise 6 degrees of freedom including X, Y, Z, and pitch, roll and yaw. In other embodiments, the Robotic sub-system may comprise further degrees of freedom, that allow the robot arm supporting base to be positioned along a linear axis running parallel to the general direction of the patient surface, and/or the supporting base height to be adjusted up or down, allowing the position of the robotic arm to be modified relative to the patient, patient surface, Cart, Coupling sub-system, additional robots/robotic arms and/or additional surgical systems, including but not limited to, surgical towers, imaging systems, endoscopic/laparoscopic systems, and/or other.

One or more robotic arms may also comprise various features to assist in maneuvering and modifying the arm position, manually or semi-manually, and of which said features may interface on or between the therapy transducer and the most distal joint of the robotic arm. In some embodiments, the feature is configured to comprise a handle allowing maneuvering and manual control with one or more hands. The handle may also be configured to include user input and electronic control features of the robotic arm, to command various drive capabilities or modes, to actuate the robot to assist in gross or fine positioning of the arm (e.g., activating or deactivating free drive mode). The work-flow for the initial positioning of the robotic arm and therapy head can be configured to allow either first positioning the therapy transducer/head in the coupling solution, with the therapy transducer directly interfaced to the arm, or in a different work-flow, allowing the user to set up the coupling solution first, and enabling the robot arm to be interfaced to the therapy transducer/coupling solution as a later/terminal set up step.

In some embodiments, the robotic arm may comprise a robotic arm on a laparoscopic, single port, endoscopic, hybrid or combination of, and/or other robot, wherein said robot of the system may be a slave to a master that controls said arm, as well as potentially a plurality of other arms, equipped to concurrently execute other tasks (vision, imaging, grasping, cutting, ligating, sealing, closing, stapling, ablating, suturing, marking, etc.), including actuating one or more laparoscopic arms (and instruments) and various histotripsy system components. For example, a laparoscopic robot may be utilized to prepare the surgical site, including manipulating organ position to provide more ideal acoustic access and further stabilizing said organ in some cases to minimize respiratory motion. In conjunction and parallel to this, a second robotic arm may be used to deliver non-invasive acoustic cavitation through a body cavity, as observed under real-time imaging from the therapy transducer (e.g., ultrasound) and with concurrent visualization via a laparoscopic camera. In other related aspects, a similar approach may be utilized with a combination of an endoscopic and non-invasive approach, and further, with a combination of an endoscopic, laparoscopic and non-invasive approach.

Coupling

Systems may comprise a variety of Coupling sub-system embodiments, of which are enabled and configured to allow acoustic coupling to the patient to afford effective acoustic cavitation/histotripsy (e.g., provide acoustic medium between transducer and patient, and support of). These may include different form factors of such, including open and enclosed solutions, and some arrangements which may be configured to allow dynamic control over the acoustic medium (e.g., temperature, dissolved gas content, level of particulate filtration, sterility, etc.). Such dynamic control components may be directly integrated to the system (within the Cart), or may be in communication with the system, but externally situated.

The Coupling sub-system typically comprises, at a minimum, coupling medium, a reservoir/container to contain said coupling medium, and a support structure. In most embodiments, the coupling medium is water, and wherein the water may be conditioned before or during the procedure (e.g., chilled, degassed, filtered, etc.). Various conditioning parameters may be employed based on the configuration of the system and it's intended use/application.

The reservoir or medium container may be formed and shaped to adapt/conform to the patient, allow the therapy transducer to engage and work within the acoustic medium, per defined and required working space (minimum volume of medium to allow the therapy transducer to be positioned and/or move through one or more treatment positions or patterns, and at various standoffs or depths from the patient, etc.), and wherein said reservoir or medium container may also mechanically support the load, and distribution of the load, through the use of a mechanical and/or electromechanical support structure. The container may be of various shapes, sizes, curvatures, and dimensions, and may be comprised of a variety of materials (single, multiple, composites, etc.), of which may vary throughout. In some embodiments, it may comprise features such as films, drapes, membranes, bellows, etc. that may be insertable and removable, and/or fabricated within. It may further contain various sensors, drains, lighting (e.g., LEDs), markings, text, etc.

In one embodiment, the reservoir or medium container contains a sealable frame, of which a membrane and/or film may be positioned within, to afford a conformable means of contacting the reservoir (later comprising the therapy transducer) as an interface to the patient, that further provides a barrier to the medium (e.g., water) between the patient and transducer). In other embodiments, the membrane and/or film may comprise an opening, the edge of which affords mechanical sealing to the patient, but in contrast allows medium communication with the patient (e.g., direct water interface with patient). The superstructure of the reservoir or medium container in both these examples may further afford the proximal portion of the structure (e.g., top) to be open or enclosed (e.g., to prevent spillage or afford additional features).

Disclosed membranes may be comprised of various elastomers, viscoelastic polymers, thermoplastics, thermoplastic elastomers, thermoset polymers, silicones, urethanes, rigid/flexible co-polymers, block co-polymers, random block co-polymers, etc. Materials may be hydrophilic, hydrophobic, surface modified, coated, extracted, etc., and may also contain various additives to enhance performance, appearance or stability. In some embodiments, the thermoplastic elastomer may be styrene-ethylene-butylene-styrene (SEBS), or other like strong and flexible elastomers.

Said materials may be formed into useful membranes through molding, casting, spraying, ultrasonic spraying and/or any other processing methodology that produces useful embodiments. They may be single use or reposable/reusable. They may be provided non-sterile, aseptically cleaned or sterile, where sterilization may comprise any known method, including but not limited to ethylene oxide, gamma, e-beam, autoclaving, steam, peroxide, plasma, chemical, etc. Membranes can be further configured with an outer molded frame to provide mechanical stability during assembly of the coupling sub-system. Various parameters of the membrane can be optimized for this method of use, including thickness, thickness profile, density, formulation (e.g., polymer molecular weight and copolymer ratios), including optimizing specifically to maximize acoustic properties, including minimizing impact to cavitation initiation threshold values, and/or ultrasound imaging artifacts, including but not limited to membrane reflections.

Open reservoirs or medium containers may comprise various methods of filling, including using pre-prepared medium or water, that may be delivered into the such, in some cases to a defined specification of water (level of temperature and gas saturation, etc.), or they may comprise additional features integral to the design that allow filling and draining (e.g., ports, valves, hoses, tubing, fittings, bags, pumps, etc.).

Enclosed iterations of the reservoir or medium container may comprise various features for sealing, in some embodiments sealing to a proximal/top portion or structure of a reservoir/container, or in other cases where sealing may comprise embodiments that seal to the transducer, or a feature on the transducer housings. Further, some embodiments may comprise the dynamic ability to control the volume of fluid within these designs, to minimize the potential for air bubbles or turbulence in said fluid. As such, integrated features allowing fluid communication, and control of, may be provided (ability to provide/remove fluid on demand), including the ability to monitor and control various fluid parameters, some disclosed above. In order to provide this functionality, the overall system, and as part, the Coupling sub-system, may comprise a fluid conditioning system, which may contain various electromechanical devices, systems, power, sensing, computing and control systems, etc.

Coupling support systems may include various mechanical support devices to interface the reservoir/container and medium to the patient, and the workspace (e.g., bed). In some embodiments, the support system comprises a mechanical arm with 3 or more degrees of freedom. Said arm may interface with one or more locations (and features) of the bed, including but not limited to, the frame, rails, customized rails or inserts, as well as one or more locations of the reservoir or container. The arm may be a feature implemented on one or more Carts, wherein Carts may be configured in various unlimited permutations, in some cases where a Cart only comprises the role of supporting and providing the disclosed support structure.

In some embodiments, the support structure and arm may be a robotically-enabled arm, implemented as a stand-alone Cart, or integrated into a Cart further comprising two or more system sub-systems, or where in the robotically-enabled arm is an arm of another robot, of interventional, surgical or other type, and may further comprise various user input features to actuate/control the robotic arm (e.g., positioning into/within coupling medium) and/or Coupling solution features (e.g., filling, draining, etc.).

Software

The system may comprise various software applications, features and components which allow the user to interact, control and use the system for a plethora of clinical applications. The Software may communicate and work with one or more of the sub-systems, including but not limited to Therapy, Integrated Imaging, Robotics and Other Components, Ancillaries and Accessories of the system.

Overall, in no specific order of importance, the software may provide features and support to initialize and set up the system, service the system, communicate and import/export/store data, modify/manipulate/configure/control/command various settings and parameters by the user, mitigate safety and use-related risks, plan procedures, provide support to various configurations of transducers, robotic arms and drive systems, function generators and amplifier circuits/slaves, test and treatment ultrasound sequences, transducer steering and positioning (electromechanical and electronic beam steering, etc.), treatment patterns, support for imaging and imaging probes, manual and electromechanical/robotically-enabling movement of, imaging support for measuring/characterizing various dimensions within or around procedure and treatment sites (e.g., depth from one anatomical location to another, etc., pre-treatment assessments and protocols for measuring/characterizing in situ treatment site properties and conditions (e.g., acoustic cavitation/histotripsy thresholds and heterogeneity of), targeting and target alignment, calibration, marking/annotating, localizing/navigating, registering, guiding, providing and guiding through work-flows, procedure steps, executing treatment plans and protocols autonomously, autonomously and while under direct observation and viewing with real-time imaging as displayed through the software, including various views and viewports for viewing, communication tools (video, audio, sharing, etc.), troubleshooting, providing directions, warnings, alerts, and/or allowing communication through various networking devices and protocols. It is further envisioned that the software user interfaces and supporting displays may comprise various buttons, commands, icons, graphics, text, etc., that allow the user to interact with the system in a user-friendly and effective manner, and these may be presented in an unlimited number of permutations, layouts and designs, and displayed in similar or different manners or feature sets for systems that may comprise more than one display (e.g., touch screen monitor and touch pad), and/or may network to one or more external displays or systems (e.g., another robot, navigation system, system tower, console, monitor, touch display, mobile device, tablet, etc.).

The software, as a part of a representative system, including one or more computer processors, may support the various aforementioned function generators (e.g., FPGA), amplifiers, power supplies and therapy transducers. The software may be configured to allow users to select, determine and monitor various parameters and settings for acoustic cavitation/histotripsy, and upon observing/receiving feedback on performance and conditions, may allow the user to stop/start/modify said parameters and settings.

The software may be configured to allow users to select from a list or menu of multiple transducers and support the auto-detection of said transducers upon connection to the system (and verification of the appropriate sequence and parameter settings based on selected application). In other embodiments, the software may update the targeting and amplifier settings (e.g., channels) based on the specific transducer selection. The software may also provide transducer recommendations based on pre-treatment and planning inputs. Conversely, the software may provide error messages or warnings to the user if said therapy transducer, amplifier and/or function generator selections or parameters are erroneous, yield a fault or failure. This may further comprise reporting the details and location of such.

In addition to above, the software may be configured to allow users to select treatment sequences and protocols from a list or menu, and to store selected and/or previous selected sequences and protocols as associated with specific clinical uses or patient profiles. Related profiles may comprise any associated patient, procedure, clinical and/or engineering data, and maybe used to inform, modify and/or guide current or future treatments or procedures/interventions, whether as decision support or an active part of a procedure itself (e.g., using serial data sets to build and guide new treatments).

As a part of planning or during the treatment, the software (and in working with other components of the system) may allow the user to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. In one embodiment, the system allows a user to manually evaluate and test threshold parameters at various points. Said points may include those at defined boundary, interior to the boundary and center locations/positions, of the selected region of interest and treatment area/volume, and where resulting threshold measurements may be reported/displayed to the user, as well as utilized to update therapy parameters before treatment. In another embodiment, the system may be configured to allow automated threshold measurements and updates, as enabled by the aforementioned Robotics sub-system, wherein the user may direct the robot, or the robot may be commanded to execute the measurements autonomously.

Software may also be configured, by working with computer processors and one or more function generators, amplifiers and therapy transducers, to allow various permutations of delivering and positioning optimized acoustic cavitation/histotripsy in and through a selected area/volume. This may include, but not limited to, systems configured with a fixed/natural focus arrangement using purely electromechanical positioning configuration(s), electronic beam steering (with or without electromechanical positioning), electronic beam steering to a new selected fixed focus with further electromechanical positioning, axial (Z axis) electronic beam steering with lateral (X and Y) electromechanical positioning, high speed axial electronic beam steering with lateral electromechanical positioning, high speed beam steering in 3D space, various combinations of including with dynamically varying one or more acoustic cavitation/histotripsy parameters based on the aforementioned ability to update treatment parameters based on threshold measurements (e.g., dynamically adjusting amplitude across the treatment area/volume).

Other Components, Ancillaries and Accessories

The system may comprise various other components, ancillaries and accessories, including but not limited to computers, computer processors, power supplies including high voltage power supplies, controllers, cables, connectors, networking devices, software applications for security, communication, integration into information systems including hospital information systems, cellular communication devices and modems, handheld wired or wireless controllers, goggles or glasses for advanced visualization, augmented or virtual reality applications, cameras, sensors, tablets, smart devices, phones, internet of things enabling capabilities, specialized use "apps" or user training materials and applications (software or paper based), virtual proctors or trainers and/or other enabling features, devices, systems or applications, and/or methods of using the above.

System Variations and Methods/Applications

In addition to performing a breadth of procedures, the system may allow additional benefits, such as enhanced planning, imaging and guidance to assist the user. In one embodiment, the system may allow a user to create a patient, target and application specific treatment plan, wherein the system may be configured to optimize treatment parameters based on feedback to the system during planning, and where planning may further comprise the ability to run various test protocols to gather specific inputs to the system and plan.

Feedback may include various energy, power, location, position, tissue and/or other parameters.

The system, and the above feedback, may also be further configured and used to autonomously (and robotically) execute the delivery of the optimized treatment plan and protocol, as visualized under real-time imaging during the procedure, allowing the user to directly observe the local treatment tissue effect, as it progresses through treatment, and start/stop/modify treatment at their discretion. Both test and treatment protocols may be updated over the course of the procedure at the direction of the user, or in some embodiments, based on logic embedded within the system.

It is also recognized that many of these benefits may further improve other forms of acoustic therapy, including thermal ablation with high intensity focused ultrasound (HIFU), high intensity therapeutic ultrasound (HITU) including boiling histotripsy (thermal cavitation), and are considered as part of this disclosure.

In another aspect, the Therapy sub-system, comprising in part, one or more amplifiers, transducers and power supplies, may be configured to allow multiple acoustic cavitation and histotripsy driving capabilities, affording specific benefits based on application, method and/or patient specific use. These benefits may include, but are not limited to, the ability to better optimize and control treatment parameters, which may allow delivery of more energy, with more desirable thermal profiles, increased treatment speed and reduced procedure times, enable electronic beam steering and/or other features.

This disclosure also includes novel systems and concepts as related to systems and sub-systems comprising new and "universal" amplifiers, which may allow multiple driving approaches (e.g., single and multi-cycle pulsing). In some embodiments, this may include various novel features to further protect the system and user, in terms of electrical safety or other hazards (e.g., damage to transducer and/or amplifier circuitry).

In another aspect, the system, and Therapy sub-system, may include a plethora of therapy transducers, where said therapy transducers are configured for specific applications and uses and may accommodate treating over a wide range of working parameters (target size, depth, location, etc.) and may comprise a wide range of working specifications (detailed below). Transducers may further adapt, interface and connect to a robotically-enabled system, as well as the Coupling sub-system, allowing the transducer to be positioned within, or along with, an acoustic coupling device allowing, in many embodiments, concurrent imaging and histotripsy treatments through an acceptable acoustic window. The therapy transducer may also comprise an integrated imaging probe or localization sensors, capable of displaying and determining transducer position within the treatment site and affording a direct field of view (or representation of) the treatment site, and as the acoustic cavitation/histotripsy tissue effect and bubble cloud may or may not change in appearance and intensity, throughout the treatment, and as a function of its location within said treatment (e.g., tumor, healthy tissue surrounding, critical structures, adipose tissue, etc.).

The systems, methods and use of the system disclosed herein, may be beneficial to overcoming significant unmet needs in the areas of soft tissue ablation, oncology, immuno-oncology, advanced image guided procedures, surgical procedures including but not limited to open, laparoscopic, single incision, natural orifice, endoscopic, non-invasive, various combination of, various interventional spaces for catheter-based procedures of the vascular, cardiovascular and/or neuro-related spaces, cosmetics/aesthetics, metabolic (e.g., type 2 diabetes), plastics and reconstructive, ocular and ophthalmology, gynecology and men's health, and other systems, devices and methods of treating diseased, injured, undesired, or healthy tissues, organs or cells.

Systems and methods are also provided for improving treatment patterns within tissue that can reduce treatment time, improve efficacy, and reduce the amount of energy and prefocal tissue heating delivered to patients.

Use Environments

The disclosed system, methods of use, and use of the system, may be conducted in a plethora of environments and settings, with or without various support systems such as anesthesia, including but not limited to, procedure suites, operating rooms, hybrid rooms, in and out-patient settings, ambulatory settings, imaging centers, radiology, radiation therapy, oncology, surgical and/or any medical center, as well as physician offices, mobile healthcare centers or systems, automobiles and related vehicles (e.g., van), and/or any structure capable of providing temporary procedure support (e.g., tent). In some cases, systems and/or sub-systems disclosed herein may also be provided as integrated features into other environments, for example, the direct integration of the histotripsy Therapy sub-system into a MRI scanner or patient surface/bed, wherein at a minimum the therapy generator and transducer are integral to such, and in other cases wherein the histotripsy configuration further includes a robotic positioning system, which also may be integral to a scanner or bed centered design.

Coordination Between Imaging and Robotics Subsystems

To effectively treat tissue with histotripsy ultrasound therapy, the ultrasound focus of the therapy system needs to be precisely placed to the target tissue (e.g., tumor and clot) inside the body. For a non-invasive treatment such as histotripsy, precise targeting can be guided by real-time imaging such as ultrasound or MRI. The advantage of using ultrasound imaging is that ultrasound is low-cost, widely available, and can visualize cavitation from the histotripsy clearly. However, ultrasound imaging has many limitations in histotripsy therapy, including: 1) Many clinical targets such as tumors may not be viewed clearly on ultrasound, 2) native Ultrasound imaging is typically 2D and does not provide precise 3D volume information of the tissue, 3) Targets inside the brain cannot be imaged with ultrasound due to the skull and limitations in acoustic windows required for imaging.

Histotripsy targeting can also be guided with real-time MRI. Tumor and clots can be viewed on MRI clearly, and MRI commonly provides 3D imaging. However, real-time MRI guidance also has limitations in histotripsy therapy, including: 1) High cost of the MRI scan time, 2) Requirement of specialized MRI-compatible and directly integrated histotripsy equipment, and 3) Limited MRI scanner availability.

The present disclosure hereby describes novel approaches for histotripsy targeting that do not require real-time imaging. Systems and methods are described herein that achieve precise targeting based on imaging scans (e.g., MRI or CT) taken prior to, or during, the treatment. The approaches described herein may include combining histotripsy with a surgical navigation capabilities and/or systems, stereotactic setup, and/or inserted fiducial markers.

The methods and systems of histotripsy targeting based on prior imaging scans can leverage the capability of MRI/CT for 3D imaging and clear visualization of tumor/clot contrast. These techniques use software and hardware components that may interact and communicate/interface with a histotripsy system, or as part of a histotripsy system, but that do not require a specialized histotripsy system wherein the system requires the physical and electromechanical integration of MRI/CT. In some embodiments, as only imaging scans prior to treatment are used, these techniques do not require real-time MRI/CT during the entire duration of the treatment, thus significantly reducing the cost of therapy while maintaining a high targeting accuracy. In some embodiments, the histotripsy system may communicate and interact with the interoperative MRI/CT, but in working in concert only (not integrated as part of the scanner itself).

The histotripsy targeting systems and methods described herein generally require a specific set of hardware and software systems which may be configured in a variety of ways, including but not limited to a histotripsy therapy transducer, a robotic positioning system coupled to the histotripsy therapy transducer and configured to control and move the position and orientation of the histotripsy therapy transducer during therapy, a surgical navigation system or sub-system, capable of producing variable-resolution (low or high) images of a target tissue volume, and prior high-resolution imaging scans of the target tissue volume such as imaging scans from a MRI or CT system. For example, the histotripsy therapy transducer and robotic positioning arm described herein (in FIG. 1) can be used for these novel targeting systems and methods. Any surgical navigation system can be used, but generally the surgical navigation system can be further configured to obtain low-resolution images of the target tissue volume, such as ultrasound or still camera images. The robot and navigation systems/sub-systems may be used to further register the robot encoded positional data, low resolution real-time images (e.g., ultrasound or optical camera), to the MRI/CT pre-procedure images, to afford real-time navigation in the MRI/CT. In some embodiments, and as previously described herein, the MRI/CT data may be registered using rigid and/or elastic and deformable models, to best fit the pre-op imaging data with the real-time data, to achieve the highest accuracy registration possible with minimal MRI/CT to body divergence.

Figure 2:
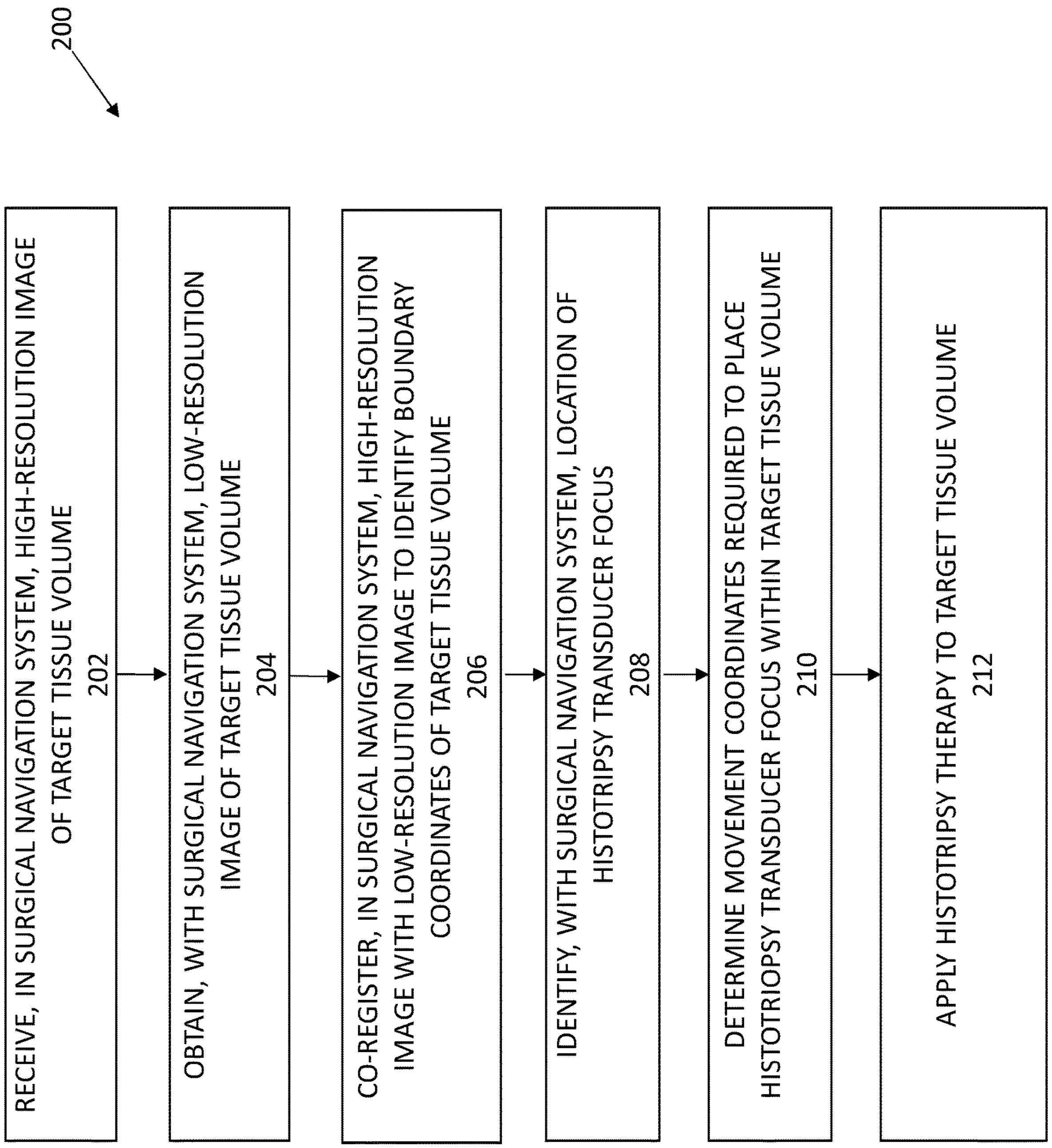
FIG. 2 is a flowchart that describes one method for surgical navigation with a histotripsy therapy system.

FIG. 2 depicts a flowchart 200 that describes steps for some representative embodiments, for performing histotripsy targeting and therapy using the system components described above, including a histotripsy therapy transducer, a robotic positioning system, and a surgical navigation system. At step 202 of flowchart 200, the surgical navigation system can receive or access prior high-resolution image(s) of the patient including a target tissue volume on or within the patient. The high-resolution image(s) can comprise, for example, 2D or 3D MRI or CT scans, cone beam CT, augmented fluoroscopy images, etc., of the patient including the target tissue volume. These images may be anatomically segmented and reconstructed into various 2D or 3D models, including deformation models accounting for any divergence or shift due to coupling or other pre/peri-procedural anatomical changes. The target tissue volume can comprise, for example, diseased or abnormal tissue such as a tumor or cancerous growth, clots, polyps, nodules, organs, etc.

Next, at step 204, the surgical navigation system can obtain a low-resolution image(s) of the target tissue volume. Typically, surgical navigation systems have their own imaging systems that can include optical imaging, near-infrared, confocal, coherence tomography, photographic, ultrasonic, etc. Thus, for purposes of discussion in this disclosure, "high-resolution image(s)" generally refers to the types of images obtained by advanced medical imaging and diagnostic systems including MRI and CT. These images can be 2D or 3D images, or further post-processed including various segmentation, reconstruction, deformation, etc. Furthermore, "low-resolution image(s)" as discussed herein generally refers to the types of images obtained with more ubiquitous, less detailed imaging and diagnostic systems such as diagnostic ultrasound and still image/camera/optical imaging.

Next, at step 206 of flowchart 200, the surgical navigation system or sub-system can be configured to localize the target tissue volume by co-registering the lower-resolution image(s) generated with the surgical navigation system/sub-system with the higher-resolution image(s) previously obtained (e.g., prior or peri-operative CT or MRI image(s)). Co-registering the images from the navigation system with the prior CT/MRI images allows the navigation system to correlate the coordinate systems between the images to identify the precise location of the target tissue volume in 2D or 3D space. In some examples, the low-resolution image(s) generated with the surgical navigation system can comprise ultrasound images, wherein the ultrasound probe is located in fixed geometry within, and relative to the histotripsy transducer, or in other embodiments the low-resolution images can comprise a digital optical image of the patient's skin surface with identifying landmarks. Co-registering the low-resolution image(s) with the high-resolution image(s) can include, at a high level, identifying a landmark or fiducial region in both the high-resolution image(s) and the low-resolution image(s) and using the landmark or fiducial region (e.g., certain features on the skull or face co-registering the brain scans) to correlate a coordinate system of the high-resolution image with a coordinate system of the low-resolution image. Since the low-resolution image may be obtained with the navigation system itself and using the robot, then the navigation system can use this correlation of coordinate systems (base to tool) to effectively navigate using the high-resolution image(s), where the robotic encoded positional data is registered to the imaging data sets. The register work-flow as presented in the system user interface may comprise fully automated work-flows, partially automated or fully manual procedure steps. Further, given histotripsy produces highly visible treatment zones, the treatment itself, as visualized by ultrasound, MRI and/or CT, may be further used peri-procedurally to update/enhance registration as needed or desired as well.

Next, at step 208 of flowchart 200, the surgical navigation system or sub-system can identify the location of the histotripsy transducer focus. In some examples, the surgical navigation can use the position and orientation of the histotripsy transducer itself, combined with the focal distance of the transducer, to determine the location of the focus. Many techniques can be used to identify the location of the histotripsy transducer focus, including placing fiducial markers (e.g., optical, electrical, or magnetic) on the transducer and identifying those fiducial markers with the surgical navigation system. By placing fiducial markers on the histotripsy ultrasound transducer that the surgical navigation system can detect, the position of the histotripsy transducer can be recognized in the coordinate system of the surgical navigation system. In one example, the fiducial markers can comprise a set of markers with a unique constellation to a known tool/device. A unique marker constellation (e.g., five sphere optical markers arranged in a specific pattern, such as the optical tracking markers for Stealth Station or Brainlab surgical navigation system) can be attached to the surface of the histotripsy transducer that can be detected by the surgical navigation system (e.g., by imaging or sensing the markers). As such, the surgical navigation system can then automatically locate and identify the histotripsy focal location on the surgical navigation system co-ordinates based on the marker constellation location/orientation and the histotripsy transducer focal length. In other embodiments, given the known geometries and predicted focal length of the transducer, a peri-procedural scan may be used to predict location using the robotic position encoder data (and pose relative to image set), to predict the ultimate bubble cloud location.

Next, at step 210 of flowchart 200, the surgical navigation system, or the robotic positioning system that controls the position and motion/movement of the histotripsy transducer, can then calculate the movement coordinates that are needed to place the histotripsy focus onto the target tissue volume. These movement coordinates are then input to the robotic positioning system to move the histotripsy transducer accordingly, and can reconcile base/tool coordinate systems. In some embodiments, software watchdogs may monitor position and pose to verify the planned versus actual location/position are accurate. In additional embodiments, movement of the histotripsy therapy focus can be achieved with a combination of electronic steering of the focus with the transducer (phased array) and mechanical movement of the transducer with the robotic positioning system.

At step 212, when the histotripsy transducer is in the proper position (e.g., the focus is located on or within the target tissue volume as verified using registered real-time and virtual imaging data), histotripsy therapy can be applied to the target tissue volume with the histotripsy therapy transducer. Typically, the target tissue is a volume, for example, a volume of tumor or a clot. To treat a target volume, the user can outline and contour the target tissue volume boundaries on the high-resolution MRI/CT scans.

For example, the surgical navigation system can include input features that allows the user to define a positive margin (e.g., a treatment margin that extends beyond or is larger than the target tissue volume, such as for treating a cancerous tumor) or a negative margin (e.g., a treatment margin that is within or smaller than the target tissue volume, such as for treating a clot) and the extent of the treatment margin (e.g., 1 cm). For example, if a tumor is the target tissue volume, the treatment margin can cover the entirety of the tumor with a margin pre-defined by the user surrounding the tumor to ensure that all the tumor cells are treated. If, for example, a clot is the target tissue volume, the treatment margin can cover a majority of the clot but leave the rim of the clot untreated to prevent damage to the surrounding normal tissue as defined by the user. After the treatment margin is defined, the surgical navigation system or the robotic arm can calculate and create treatment parameters to cover the target tissue volume and display the treatment margins overlaid on the prior MRI/CT scans of the patient. Fine tuning or further adjustments to the treatment margin or coordinates can be made if desired by the user. The treatment margin location coordinates can then be fed to the robotic control system to move the histotripsy transducer accordingly to deliver the treatment, including through desired pathway, pattern, direction and order, and including any determined cooling and/or off-time (to prevent any non-target tissue effect). These parameters may be further displayed through one or more user interfaces and displays as previously disclosed herein.

Stereotactic Histotripsy

Figure 3:
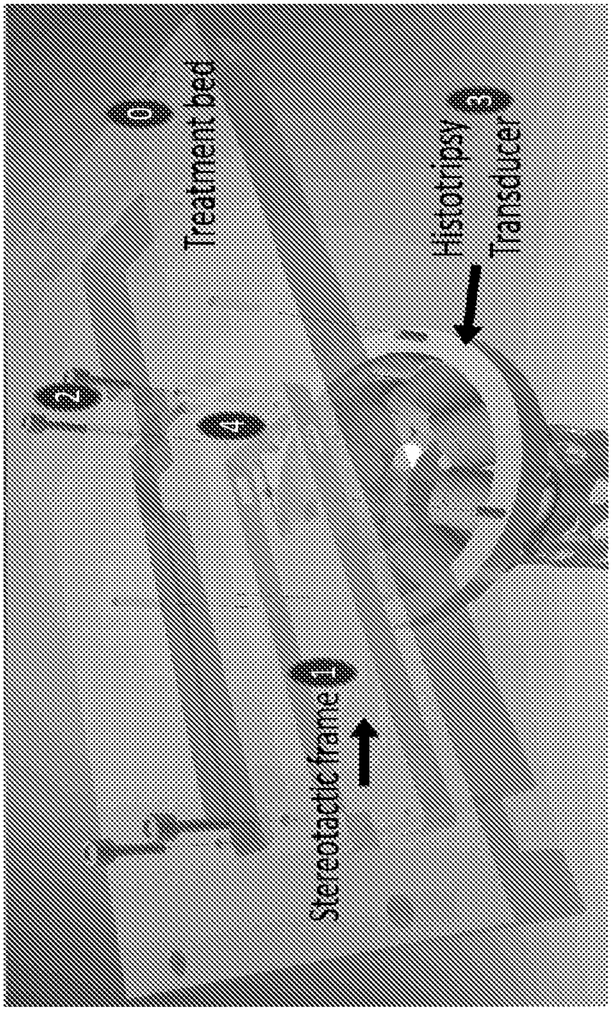
FIG. 3 is one example of a stereotactic histotripsy therapy system.

Another embodiment for histotripsy targeting uses a stereotactic approach. Similar to the approach described above in FIG. 2 with the surgical navigation system, targeting using stereotactic histotripsy also relies on prior MRI or CT scans of the patient and while it may use real-time imaging, it does not require it. However, stereotactic histotripsy requires a stereotactic frame for targeting. FIG. 3 illustrates one embodiment of a stereotactic histotripsy treatment system, which can include a treatment bed 0, a stereotactic frame 1, a histotripsy therapy transducer 3, and one or more fiducial markers 4. Referring to FIG. 3, the stereotactic frame 1 can be attached to the treatment bed, and the histotripsy transducer can be affixed to the stereotactic frame. The histotripsy transducer must be in a fixed position relative to the stereotactic frame, such that the position/orientation of the histotripsy therapy transducer is always known with respect to the position of the stereotactic frame.

Figure 4C:
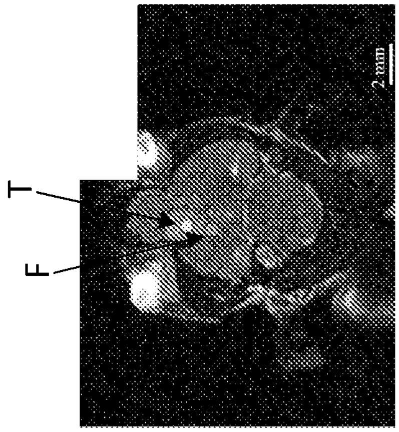
FIGS. 4A-4C illustrate a method of performing stereotactic histotripsy.
Figure 4B:
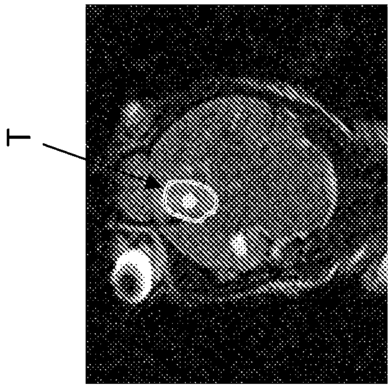
Figure 4A:
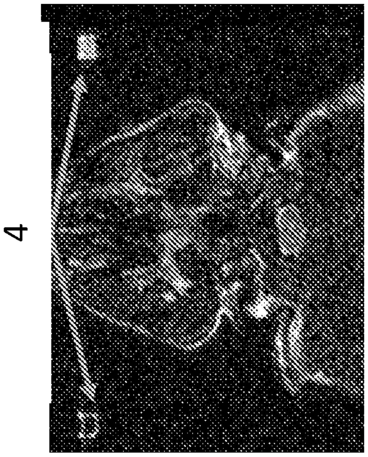

In most examples, the stereotactic frame can be rigidly mounted to the patient's head or torso depending on the target tissue volume. MRI or CT scans of the patient and the target tissue volume can be obtained with the stereotactic frame prior to treatment. Since the stereotactic frame includes fiducial markers that are detectable by MRI or CT, those fiducial markers will be imaged in the pre and/or peri procedural MRI or CT scans (See fiducial markers 4 in FIG. 4A). Based on these scans, the locations of the fiducial markers with regard to the tumor locations T can be localized based on the positions of the fiducial markers (See FIG. 4B). The histotripsy transducer can then be mechanically mounted to the stereotactic frame, such that the location of the histotripsy transducer and focus will be known with regard and relative to the fiducial markers on the stereotactic frame. With these conditions satisfied, the robotic positioning control system that controls the histotripsy transducer and its position, location and motion, and the histotripsy system software, can calculate or determine the location of the current histotripsy focus F with regard to the target tissue volume and target/region of interest (See FIG. 4C). The robotic positioning system can then be used to move the therapy transducer to align the histotripsy focus to the target location(s).

When the target tissue volume is a tumor, the locations of the tumor boundary can be outlined and contoured on the pre or peri-procedural MRI or CT scans, and the tumor boundary coordinates with regard to the fiducial markers and the current histotripsy focus can be calculated by the robotic positioning and histotripsy system. As described above, the system can be configured to allow the user to define positive vs. negative treatment margins (e.g., positive margin to extend beyond the tumor or negative margin to treat within the clot) and the extent of the margin (e.g., 1 cm). After the treatment margin is defined, the system can calculate and create 3D grid locations to cover the target tissue volume and display the 3D grid locations overlaid on prior MRI/CT scans of the patient. If the user believes that adjustment of the grid locations is needed, he/she can make adjustment to the treatment margin or coordinates on the fly. In some embodiments, adjustments may be made using elastic and deformation models to further visualize grid and planned cloud locations in the most clinically relevant image sets. Once the user confirms the coordinates, the 3D grid location coordinates are then fed to the robotic positioning system and software to move the histotripsy transducer accordingly to deliver the treatment per the defined plan, including but not limited to the pattern, pathway and any predetermined cooling and/or off-times to manage prefocal thermal or other undesired tissue effects. In addition to robotic mechanical delivery, the system may use electronic focal steering in part, or full, to deliver the desired plan, including any treatment planning steps (e.g., test pulses) and/or therapy itself (e.g., full volumetric ablation).

Targeting with Catheter Insertion

In certain treatments, insertion of a catheter or needle is needed. One example is the treatment of intracerebral hemorrhage, where a catheter is typically used to drain a clot liquefied by histotripsy therapy. In this example, a catheter or needle is inserted into the target tissue. The insertion of the needle or catheter can be guided by a surgical navigation system or some form of imaging as routinely performed clinically. To guide the catheter or needle during therapy, the tip of the catheter or needle with regard to the boundary of the target tissue volume should be known at the point of insertion. In one embodiment, the tip of the catheter or needle can include an acoustic detector and/or source, configured to receive or emit, ultrasound signals from the and/or measured by, the histotripsy transducer, respectively. Alternatively, the catheter or needle can include fiducial markers. These ultrasound signals or fiducial markers can be used to localize the position of the target tissue volume relative to the position of the histotripsy transducer. The robotic positioning system that controls movement of the histotripsy transducer can then calculate the coordinates of the histotripsy transducer or focus with regard to the catheter tip, and thus the target tissue. The robotic positioning system can then calculate the movement coordinates required to align the histotripsy focus onto the target tissue volume. Treatment margins of can be calculated and adjusted, as described above. Further, if a peri-procedural image set (MRI or CT) is captured, including catheter location, the robotic encoder positional data may be used to further register this data stream to the acoustic data to further enhance registration accuracy.

Targeting with Marker Insertion

For cases that do not require catheter or needle insertion, it is also possible to implant fiducial markers at the time of biopsy either inside or near the target tissue volume. These fiducial markers can then be visualized on MRI or CT. These markers can also preferable be ultrasound reflective to allow the histotripsy transducer to receive acoustic reflection signals from these markers to localize these markers during therapy. This allows the histotripsy therapy system to identify the coordinates of the current histotripsy focus with regard to the fiducial markers in real-time. Based on the locations of the markers relative to the target tissue volume, the treatment margin coordinates relative to the current histotripsy focus will be calculated. The target tissue volume can be treated using the techniques described above.

Figure 5:
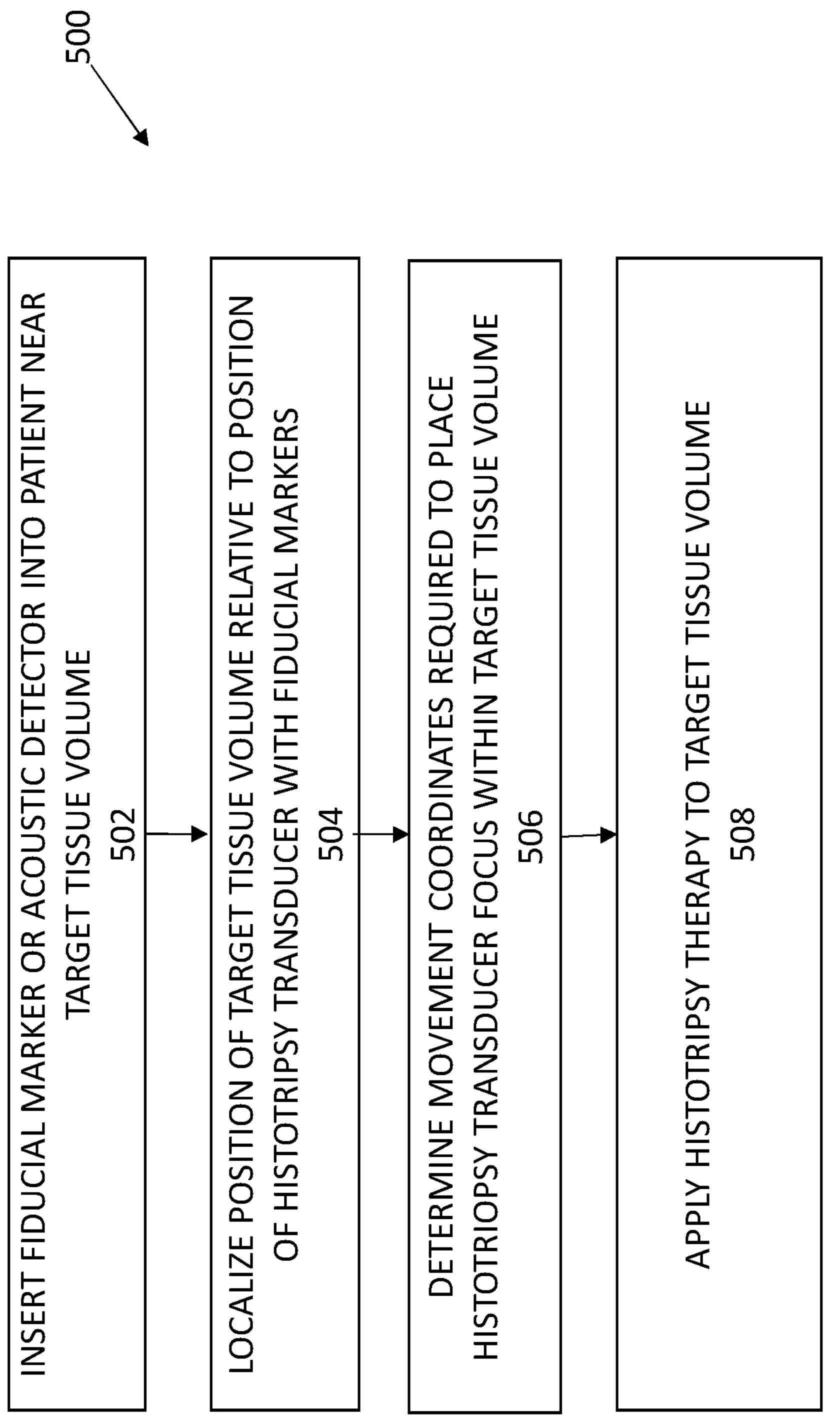
FIG. 5 is a flowchart that describes another method for surgical navigation with a histotripsy therapy system.

Referring to FIG. 5, a flowchart 500 is provided that describes steps for some representative embodiments, for performing histotripsy targeting and therapy using the system components described above, including a histotripsy therapy transducer, a robotic positioning system, and/or a surgical navigation system.

At step 502 of flowchart 500, the method can include inserting a fiducial marker or acoustic detector into a patient near the tissue volume. As described above, in some embodiments a surgical procedure can include inserting a catheter or a needle near a target tissue site. The catheter or needle can include, for example, fiducial markers disposed thereon or therein as described above. Alternatively, the catheter or needle can include an ultrasound sensor or transmitter. In an alternative embodiment, fiducial markers or an acoustic sensor/transmitter can be injected into the patient's tissue within or near the target tissue site.

Next, at step 504 of flowchart 500, the method can include localizing the target tissue volume relative to the position of the histotripsy transducer. In some embodiments, localizing the position of the target tissue volume can include transmitting ultrasound energy from the histotripsy therapy transducer towards a needle or catheter in the tissue that includes an ultrasound sensor. The signals received by the ultrasound sensor can be used to determine the location of the target tissue volume relative to the histotripsy therapy transducer. In other embodiments, fiducial markers on the needle or catheter, or alternatively, fiducial markers injected into the tissue, can be used to correlate a coordinate system of the histotripsy therapy system and/or surgical navigation system to the location of the target tissue volume.

In some implementations, the surgical navigation system or sub-system can identify the location of the histotripsy transducer focus. In some examples, the surgical navigation can use the position and orientation of the histotripsy transducer itself, combined with the focal distance of the transducer, to determine the location of the focus. Many techniques can be used to identify the location of the histotripsy transducer focus, including placing fiducial markers (e.g., optical, electrical, or magnetic) on the transducer and identifying those fiducial markers with the surgical navigation system. By placing fiducial markers on the histotripsy ultrasound transducer that the surgical navigation system can detect, the position of the histotripsy transducer can be recognized in the coordinate system of the surgical navigation system. In one example, the fiducial markers can comprise a set of markers with a unique constellation to a known tool/device. A unique marker constellation (e.g., five sphere optical markers arranged in a specific pattern, such as the optical tracking markers for Stealth Station or Brainlab surgical navigation system) can be attached to the surface of the histotripsy transducer that can be detected by the surgical navigation system (e.g., by imaging or sensing the markers). As such, the surgical navigation system can then automatically locate and identify the histotripsy focal location on the surgical navigation system co-ordinates based on the marker constellation location/orientation and the histotripsy transducer focal length. In other embodiments, given the known geometries and predicted focal length of the transducer, a peri-procedural scan may be used to predict location using the robotic position encoder data (and pose relative to image set), to predict the ultimate bubble cloud location.

Next, at step 506 of flowchart 500, the surgical navigation system, or the robotic positioning system that controls the position and motion/movement of the histotripsy transducer, can then calculate the movement coordinates that are needed to place the histotripsy focus onto the target tissue volume. These movement coordinates are then input to the robotic positioning system to move the histotripsy transducer accordingly, and can reconcile base/tool coordinate systems. In some embodiments, software watchdogs may monitor position and pose to verify the planned versus actual location/position are accurate.

At step 508, when the histotripsy transducer is in the proper position (e.g., the focus is located on or within the target tissue volume as verified using registered real-time and virtual imaging data), histotripsy therapy can be applied to the target tissue volume with the histotripsy therapy transducer. Typically, the target tissue is a volume, for example, a volume of tumor or a clot. To treat a target volume, the user can outline and contour the target tissue volume boundaries on the high-resolution MRI/CT scans. For example, the surgical navigation system can include input features that allows the user to define a positive margin (e.g., a treatment margin that extends beyond or is larger than the target tissue volume, such as for treating a cancerous tumor) or a negative margin (e.g., a treatment margin that is within or smaller than the target tissue volume, such as for treating a clot) and the extent of the treatment margin (e.g., 1 cm). For example, if a tumor is the target tissue volume, the treatment margin can cover the entirety of the tumor with a margin pre-defined by the user surrounding the tumor to ensure that all the tumor cells are treated. If, for example, a clot is the target tissue volume, the treatment margin can cover a majority of the clot but leave the rim of the clot untreated to prevent damage to the surrounding normal tissue as defined by the user. After the treatment margin is defined, the surgical navigation system or the robotic arm can calculate and create treatment parameters to cover the target tissue volume and display the treatment margins overlaid on the prior MRI/CT scans of the patient. Fine tuning or further adjustments to the treatment margin or coordinates can be made if desired by the user. The treatment margin location coordinates can then be fed to the robotic control system to move the histotripsy transducer accordingly to deliver the treatment, including through desired pathway, pattern, direction and order, and including any determined cooling and/or off-time (to prevent any non-target tissue effect). These parameters may be further displayed through one or more user interfaces and displays as previously disclosed herein.

Additional Imaging and Treatment Planning Features

In some examples, the surgical navigation system can include a modeling tool that can be used to capture the boundary mesh coordinates of the target tissue volume from the pre-treatment MRI or CT scan. These mesh coordinates can be used directly to calculate the 3D grid points of the treatment margin, which can be overlaid onto the pre-treatment MRI or CT scan. Alternatively, these mesh coordinates can be fed to the robotic arm to calculate the 3D grid points and/or histotripsy therapy controls system to provide electronical focal steering coordinates/commands, to cover target tissue volume and treatment margin.

Once the high and low-resolution images are co-registered, the surgical navigation system can be used to measure the distance between anatomical landmarks in the MRI or CT scans. For example, the surgical navigation system can measure the distance from the center of the target tissue volume and a boundary of the target volume at different axes. These distance values can be fed to the robotic arm to calculate the upper limit that can limit the maximum distance used for the steering distance for treating the target tissue volume.

Histotripsy mechanically disrupts cells to destroy the target tissue through cavitation. A histotripsy ultrasound transducer can have both transmit capability to generate cavitation and receive capability to receive emission signals from cavitation. As such, cavitation mapping generated by the histotripsy transducer during treatment in real-time can be overlaid onto prior MRI/CT scans of the patients to ensure that the treatment is within the boundary defined by the targeting. If cavitation is generated outside the outlined target volume. Treatment can be stopped. A histotripsy transducer array with transmit-receive capability can produce a 3D cavitation map (i.e., histotripsy treatment map) during treatment to indicate precisely the tissue locations that are being treated with cavitation in real-time. This cavitation map can be overlaid onto the MRI/CT scans in real time to allow the user to monitor the treatment in high-resolution in real-time. In some examples, a treatment cavitation map can be imported to the surgical navigation system or the robotic positioning system and/or overlaid onto the pre-treatment MRI/CT scans showing the planned treatment volume.

In another example, the surgical navigation system can include a "merge" feature for co-registering MRI, CT, or any other images of the same body part or anatomical landmark (e.g., head, abdomen, etc.) of the same patient, but at different orientations. Post-treatment images can be imported to co-register with pre-treatment images on the same image plan to allow accurate post-treatment volume matches with the planned treatment volume.

If the target tissue volume is a moving target, e.g., an abdominal organ with breathing motion, the motion can result in targeting errors in the systems described above. In this example, the implementation of histotripsy can be gated with the patient's respiration/ventilation, such that histotripsy is only applied when the target is at the resting position, for a fixed focus transducer. For example, an accelerometer or other sensor can be placed on the body of the patient near to the target tissue volume to detect movement and the measurements from the sensor can be fed to the histotripsy therapy system. If the system detects movement above a threshold value, delivery of histotripsy therapy can be halted or delayed until the movement value returns below the threshold value. Similarly, a simple respiratory monitor can be applied to the patient, and respiratory data can be used by the system to deliver therapy only when the patient is at the resting position. It is also possible to ask the patient to perform breath hold during the therapy delivery. If the patient is actually on a ventilator during the procedure, the therapy can be delivered when the ventilation machine delivery is below a pre-define threshold. In the case when histotripsy is delivered with a phased array transducer and the transducer focus can be moved instantaneously via electronic steering, the histotripsy focal location can be moved along with the breathing to track the moving target in real-time. For example, the location of the moving target can be estimated based on the output of an accelerometer or other sensor can be placed on the body of the patient, a respiratory monitor, or a ventilator. In another example, triggered imaging may be used, wherein the registered real-time and virtual data are used to plan treatment triggers where therapy is triggered on when the target is in a desired focal zone location, and may be also turned off when said target migrates out of the desired focal zone location.

When the targeting is based on prior CT/MRI scans using the methods described above, it should be noted that deformation of the body may occur. For example, patients may lay in a different position during the treatment compared to in a prior scan; ultrasound coupling device used to acoustically couple the histotripsy transducer to the patient's skin can also cause the patient's body to deform. In these cases, to ensure treatment accuracy, prior MRI or CT scan datasets can be processed (e.g., rotated) to co-register with the deformed elastic body parts at the treatment using the existing radiological tools.

EXAMPLES

Example 1—Histotripsy targeting with surgical navigation system. In this example, a robotic positioning system with a histotripsy therapy transducer is guided by a surgical navigation system to treat a tumor, in particular a liver tumor. The targeting can be implemented in the steps as described below.

1. Prior CT/MRI scan—As part of the diagnosis, the patient's abdomen can be scanned by CT or MRI with fine resolution prior to the treatment. Prior to the treatment, the abdomen can also be imaged with the surgical navigation system with coarse resolution (e.g., ultrasound or a digital camera).

2. Identifying the target location with surgical navigation system—Based on the prior CT or MRI scans, the surgical navigation system can be used to identify the 3D location and boundaries of the target tumor. For example, the images with coarse resolution taken with the surgical navigation system can be co-registered with the CT or MR image taken with fine resolution prior to the treatment. The tumor boundary coordinates can then be known and calculated by the surgical navigation system.

3. Identifying histotripsy transducer location—Fiducial sensors can be placed in a fixed location on or near the histotripsy therapy transducer that are detectable by the surgical navigation system. The surgical navigation system can then know the coordinates of the histotripsy transducer use those coordinates to determine the location of the histotripsy focus.

4. Align the histotripsy focus to the target tissue volume—Based on above coordinates, the movement coordinates required to move the histotripsy transducer to align the histotripsy focus to align onto a central location within the target tissue volume can be calculated by the surgical navigation system or the robotic positioning system that moves the histotripsy transducer. The robotic positioning system can then be configured to move the histotripsy transducer to align the histotripsy focus to the target tissue volume.

5. Create 3D grid coordinates to target the tumor volume with a treatment margin—The user of the system can identify the boundaries of the tumor in each slice or image of the prior MR or CT scans. The user can also input the desired treatment margin (e.g., a margin of 1 cm beyond the tumor boundary). The surgical navigation system or the robotic positioning system can then calculate and create 3D grid locations that cover the entirety of the tumor with the desired 1 cm treatment margin surrounding the tumor. The surgical navigation system or the robotic positioning system can then display the 3D grid locations overlaid onto the prior MRI/CT scans of the patient. The 3D grid location coordinates can then be fed to the robotic positioning system to move the histotripsy transducer accordingly during the treatment.

Example 2—as detailed in Example 1, but wherein the navigation system, histotripsy system and robotic delivery system are all configured as one integrated electromechanical and software controlled system and form factor.

Example 3—as detailed in Example 1 and 2, but wherein the pre-procedure MRI/CT is obtained with the coupling solution in place on the patient, so any observed MRI/CT-body divergence is calculated and known prior to planning the histotripsy ablation/treatment.

Example 4—Stereotactic histotripsy. In this example, stereotactic histotripsy is used to target a brain tumor. The targeting can be implemented in the steps as described below.

1. Prior CT/MRI scan—Prior to the treatment, a stereotactic frame can be rigidly fixed to the patient's head. The stereotactic frame can include a plurality (e.g., four) of fiducial markers. The patient's head along with the stereotactic frame can be scanned by MRI or CT to image the target tissue volume and the fiducial markers.

2. Identifying the target location—Since the CT or MRI scans visualize both the fiducial markers and the brain tumor, the location of the tumor relative to the fiducial markers is known.

3. Identifying histotripsy transducer location—A histotripsy transducer can attached to the stereotactic frame rigidly at the pre-designed connecting points, such that the location of the histotripsy transducer focus relative to the fiducial markers on the stereotactic frame is fixed and always known.

4. Align the histotripsy focus to the target—Based on the coordinates of the fiducial markers, the selected tumor center, and the histotripsy focus, the movement coordinates to move the histotripsy focus to align onto a central location within the tumor can be calculated by the robotic positioning system. The robotic positioning system can then be configured to move the histotripsy transducer to align the current histotripsy focus to the tumor center. For the brain target, the ultrasound propagates through the skull with varying thickness, which can introduce aberration and cause defocusing and reduced focal pressure. An aberration correction algorithm can be applied based on prior CT scan to improve focusing the focal pressure.

5. Create 3D grid coordinates to target the tumor volume with a margin—Once the histotripsy focus is moved to the tumor center. The user can identify the target tissue volume boundaries on each image of the MR or CT scans. Then the user can input the desired treatment margin (e.g., a margin of 1 cm beyond the tumor boundary circled out on prior MRI/CT scans). The robotic positioning system can be configured to calculate and create 3D grid locations that cover the entirety of the tumor with the 1 cm treatment margin surrounding the tumor. The robotic arm system can display the 3D grid locations overlaid on the prior MRI/CT scans of the patient.

Example 5—Histotripsy targeting with catheter insertion. In this example, histotripsy targeting can be guided by a catheter insertion, and the target treatment volume is a blood clot in the brain for the treatment of hemorrhagic stroke or intracerebral hemorrhage (ICH). For ICH treatment, histotripsy applied from outside the skull can be used to rapidly liquefy the clot, and the catheter inserted into the clot can be used to drain the clot after it is liquefied. The targeting can be implemented in the steps as described below.

1. Prior CT scan—Prior to the treatment, the patient's brain can be scanned by CT or MRI with fine resolution.

2. Catheter hydrophone insertion—The catheter hydrophone can be inserted into the center of the clot through a burr hole in the skull. The insertion can be guided by a surgical navigation system or real-time imaging. The location of the catheter tip with regard to the clot boundary should be known. This catheter can include a miniature hydrophone incorporated at the tip of its guiding wire.

3. Align the histotripsy focus to the target—This catheter hydrophone can be used to measure the ultrasound signal from the histotripsy ultrasound array elements. The signals can be used to calculate the ultrasound travel time from each histotripsy array element to the catheter hydrophone. Based on the hydrophone signals, and the location of the catheter tip with regard to the current histotripsy focus can be calculated, and aberration correction can be performed. The robotic arm system can then use these coordinates to move the histotripsy transducer to align the histotripsy focus to the catheter tip.

4. Create 3D grid coordinates to target the clot volume—The user can identify the clot boundaries in each image of MR or CT scans. To avoid damage to the normal brain tissue surrounding the clot, the clinician can input a desired negative margin (e.g., liquefying the clot with histotripsy but leaving a margin of ~5 mm rim of intact clot). The robotic positioning system can then calculate and create 3D grid locations that would cover the entirety of the clot while leaving a ~5 mm clot margin to preserve the normal brain tissue surrounding the clot. The robotic positioning system can also be configured to display the 3D grid locations overlaid on prior MRI/CT scans.

Other Systems and Methods of Use

The systems and methods described herein are related to the systems and methods described in International Application No. PCT/US2019/063728, filed Nov. 27, 2019, which is incorporated herein by reference. Any of the systems described herein can be further configured to perform the methods described in International Application No. PCT/US2019/063728.

What is claimed is:

1. A method of surgical navigation, comprising:

receiving, in a surgical navigation system comprising a histotripsy therapy transducer and an ultrasound imaging probe coupled to a robotic arm, a first image of a target tissue volume from a first imaging modality;

positioning the histotripsy therapy transducer and the ultrasound imaging probe within an acoustic coupling medium near the target tissue volume;

adjusting an axial position of the ultrasound imaging probe relative to the histotripsy therapy transducer to modify a distance between the ultrasound imaging probe and the target tissue volume;

tracking the axial position of the ultrasound imaging probe relative to the histotripsy therapy transducer with an encoder;

obtaining, with the ultrasound imaging probe, a second image of the target tissue volume;

co-registering, in the surgical navigation system, the first image with the second image to correlate a first coordinate system of the first imaging modality with a second coordinate system of the ultrasound imaging probe and to identify boundary coordinates of the target tissue volume in the first image;

identifying, with the surgical navigation system, focal coordinates of a focus of the histotripsy therapy transducer;

determining, in the surgical navigation system, movement coordinates that will place the histotripsy therapy transducer focus within the boundary coordinates of the target tissue volume in the first image using the axial position of the ultrasound imaging probe tracked with the encoder; and controlling the robotic arm to move the histotripsy therapy transducer focus based on the movement coordinates to place the histotripsy therapy transducer focus within the target tissue volume.

2. The method of claim 1, further comprising electronically steering the histotripsy therapy transducer focus within the target tissue volume.

3. The method of claim 1, wherein the first image comprises a MRI image.

4. The method of claim 1, wherein the first image comprises a CT image.

5. The method of claim 1, wherein the second image comprises an ultrasound image.

6. The method of claim 1, wherein the co-registering step further comprises identifying a fiducial region in both the first image and the second image and using the fiducial region to correlate the first coordinate system with the second coordinate system.

7. The method of claim 1, wherein identifying focal coordinates further comprises placing fiducial markers on the histotripsy therapy transducer and identifying the fiducial markers with the surgical navigation system.

8. The method of claim 1, further comprising:

defining a treatment margin of the target tissue volume;

calculating 3D grid locations to cover the target tissue volume and the treatment margin; and displaying the 3D grid locations over the first or second image.

9. The method of claim 8, wherein the treatment margin comprises a positive treatment margin that extends beyond the target tissue volume.

10. The method of claim 8, wherein the treatment margin comprises a negative treatment margin that extends within the target tissue volume.

11. The method of claim 1, further comprising applying histotripsy therapy to the target tissue volume.

12. The method of claim 11, further comprising imaging the histotripsy therapy and peri-procedurally updating co-registration between the first image and the second image.

13. The method of claim 1, further comprising producing a histotripsy treatment map; and overlaying the histotripsy treatment map on the first or second image in real time.

14. The method of claim 1, wherein the robotic arm can move the histotripsy therapy transducer with 3 degrees of freedom.

15. The method of claim 1, wherein the robotic arm can move the histotripsy therapy transducer with 6 degrees of freedom.

16. The method of claim 1, wherein the first image comprises a cone beam CT image.

* * * * *